(12) United States Patent
Shin et al.

(10) Patent No.: US 10,738,006 B2
(45) Date of Patent: Aug. 11, 2020

(54) METHOD FOR OXYGENATIVE COUPLING OF ALKYNES USING ACID CATALYST

(71) Applicant: Industry-University Cooperation Foundation Hanyang University, Seoul (KR)

(72) Inventors: Seunghoon Shin, Seoul (KR); Dilip V. Patil, Seoul (KR); Seung Woo Kim, Seoul (KR); Quynh H. Nguyen, Seoul (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 0 days.

(21) Appl. No.: 15/925,555

(22) Filed: Mar. 19, 2018

(65) Prior Publication Data

US 2018/0282273 A1    Oct. 4, 2018

(30) Foreign Application Priority Data

Mar. 20, 2017 (KR) .......................... 10-2017-0034372

(51) Int. Cl.
| | |
|---|---|
| *C07D 209/24* | (2006.01) |
| *C07C 213/08* | (2006.01) |
| *C07C 231/10* | (2006.01) |
| *C07C 231/14* | (2006.01) |

(52) U.S. Cl.
CPC .......... *C07D 209/24* (2013.01); *C07C 213/08* (2013.01); *C07C 231/10* (2013.01); *C07C 231/14* (2013.01)

(58) Field of Classification Search
CPC .................................................. C07D 209/24
See application file for complete search history.

(56) References Cited

PUBLICATIONS

Patil et al., Angewandte Chemie International Edition, published online Feb. 23, 2017, 56(13), pp. 3670-3674. (Year: 2017).*
Kalsi, P.S. Organic Reactions and Their Mechanisms, 2nd Ed. New Delhi: New Age International (P) Limited Publishers, 2000, pp. 83, 84, and 86. (Year: 2000).*
Miran, M., Kinoshita, H., Yasuda, T., Bin Hasan Susan, M., Dokko, K., & Watanabe, M. (2012). Protic Ionic Liquids Based on a Super-Strong Base: Correlation between Physicochemical Properties and ΔpKa. MRS Proceedings, 1473, Mrss12-1473-bbb06-09. doi:10.1557/opl.2012.1133. (Year: 2012).*
Weimer et al. Organometallics, 2016, 35, pp. 1202-1208. (Year: 2016).*
Chen et al., "Metal-Free Oxidation/C(sp$^3$)-H Functionalization of Unactivated Alkynes Using Pyridine-N-Oxide as the External Oxidant", Angew. Chem. Int. Ed. 2012, 51, 12307-12310.
He et al., "Electrophilicity of α-oxo gold carbene intermediates: halogen abstractions from halogenated solvents leading to the formation of chloro/bromomethyl ketones", Org. Biomol. Chem., 2012, 10, 3168, 4 pages.
Kim, Seung Woo et al., "Bronsted acid-catalyzed α-halogenation of ynamides from halogenated solvents and pyridine-N-oxides", Chem. Commun., 2017, 53, 2733-2736.
Kim, Seung Woo et al., Supporting evidence of publication date for: "Bronsted acid-catalyzed α-halogenation of ynamides from halogenated solvents and pyridine-N-oxides", Chem. Commun., 2017, 53, 2733-2736, http://pubs.rsc.org/en/content/articlelanding/2017/cc/c6cc10286g, retrieved on Jan. 29, 2018, 5 pages.
Kim et al., "Bronsted Acid-Catalyzed α-Halogenation of Ynamides from Halogenated Solvents and Pyridine-N-Oxides", Chem. Commun., 2017, 53, 1-4.
Office Action of Korean patent application 10-2017-0034372, 12 pages (in Korean language, referenced cited in English), 2017.
Patil, Dilip V., (Powerpoint published Nov. 17, 2016), "Access to α,α-Diarylated Carbonyl compounds by virtue of Bronsted Acid-Catalyzed Activation of Ynamides Under Mild Conditions", Materials of the seminar at Hanyang University.
Patil, Dilip V. et al., (Poster published Dec. 12, 2016) "Access to α,α-Diarylated Carbonyl compounds With Virtue of Bronsted Acid-Catalyzed Activation of Ynamides Under Mild Conditions", Poster presented at 21$^{st}$ International Conference on Organic Synthesis, Dec. 11-16, 2016, Mumbai, India.
Patil, Dilip V. et al., (Poster published Aug. 22, 2016), "Bronsted Acid-Catalyzed Bis-functionalization of Ynamides: Access to α,α-Diarylated Carbonyl Compounds", Poster presented in Seoul, Korea.
Patil, Dilip V. et al., "Bronsted Acid-Catalyzed Oxygenative Biomolecular Friedel-Crafts-type Coupling of Ynamides", Angew. Chem. Int. Ed., Published Feb. 23, 2017, 56:1-6.
Shin, Seunghoon, (Powerpoint published Jan. 11, 2017), "Engaging Ynamides in Bronsted Acid Catalysis", Materials of the seminar at Hanyang University.

* cited by examiner

*Primary Examiner* — Laura L Stockton
(74) *Attorney, Agent, or Firm* — Sughrue Mion, PLLC

(57) ABSTRACT

The present disclosure relates to a method for preparing various physiologically active pharmaceutical ingredients, such as a 1,1-diaryl compound and a 1,1-diheteroaryl compound (specifically, a 1,1-diaryl carbonyl compound), in an economical and convenient manner under mild conditions without using an expensive transition metal catalyst by activating an alkyne compound (e.g., an ynamide) using a Brønsted acid as a catalyst to induce a reaction of the activated alkyne compound and a N—O bond oxidant to form an adduct intermediate and then inducing a coupling reaction of the adduct intermediate with various nucleophilic organic compounds (e.g., a nucleophilic arene compound).

18 Claims, 18 Drawing Sheets

METHOD FOR OXYGENATIVE COUPLING OF ALKYNES USING ACID CATALYST

CROSS-REFERENCE TO RELATED APPLICATION

This application claims priority to and the benefit of Korean Patent Application No. 10-2017-0034372, filed on Mar. 20, 2017, the disclosure of which is incorporated herein by reference in its entirety.

FIELD OF THE INVENTION

The present disclosure relates to a method for performing an oxygenative coupling reaction of alkyne compounds using an acid catalyst. More specifically, the present disclosure relates to a method for preparing various physiologically active pharmaceutical ingredients, such as 1,1-diaryl compounds, 1,1-diheteroaryl compounds, and 1,4-dicarbonyl compounds, in an economical and convenient manner under mild conditions without using an expensive transition metal catalyst by activating an alkyne compound (e.g., an ynamide) using a Brønsted acid as a catalyst to induce a reaction of the activated alkyne compound and a N—O bond oxidant to form an adduct intermediate and then inducing a coupling reaction of the adduct intermediate with various nucleophilic organic compounds (e.g., a nucleophilic arene compound).

DESCRIPTION OF THE PRIOR ART

As an interest of the synthesis of 1,1-diaryl compounds (e.g., chiral 1,1-diaryl compounds) has recently increased, related studies have been actively conducted. Specifically, organic compounds having a 1,1-diaryl structure exhibit various physiological activities, and examples thereof are known to include antihistamines, antiarrhythmics, diuretics, antidepressants, emollients, topical anesthetics, anticholinergics, antimuscarinics, endothelin antagonists, and the like (e.g., UK-350,926 from Pfizer).

It is known that for the synthesis of 1,1-diaryl compounds, diazo compounds are decomposed by a transition metal (Rh, Cu, etc.)-catalyzed reaction to form a carbene intermediate. The synthesis of 1,1-diaryl compounds using diazo compounds has the risk of explosion and toxicity, and thus, a reaction mechanism in which a carbene is formed by an oxygenative reaction of alkyne compounds, specifically, ynamide compounds using a N—O bond oxidant in the presence of a gold catalyst has been recently developed (Zhang et al., Org. Biomol. Chem., 2012, 10, 3168).

In this connection, the foregoing reaction mechanism of the conventional art may be described as shown in Reaction Scheme 1.

[Reaction Scheme 1]

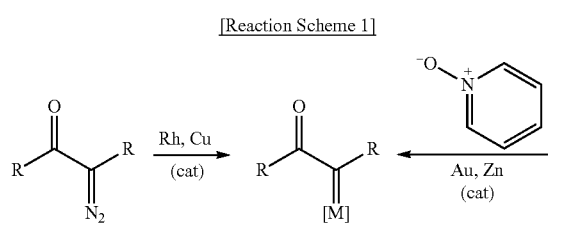

However, the methods using metal-carbene intermediates have the following disadvantages. That is, the carbene intermediates exhibit various and favorable reactive characteristics, but the carbene intermediates are very unstable and require very vigorous reaction conditions. In addition, these methods involve the use of transition metals, and thus are difficult to apply in the manufacture of pharmaceutical products, which must satisfy strict regulations on residual metals, and the synthesis of materials, in which a trace amount of metal impurities may be problematic. Also, the kinds of nucleophiles applicable in the coupling reaction are limited, and thus, various 1,1-diaryl compounds and the like are difficult to synthesize.

Meanwhile, in order to solve the limitation of the conventional art using metal catalysts for the reaction of alkyne compounds, a reaction route not using a metal has been proposed as shown in Reaction Scheme 2 below (Gong et al., Angew. Chem. Int. Ed. 2012, 51, 12307-12310).

[Reaction Scheme 2]

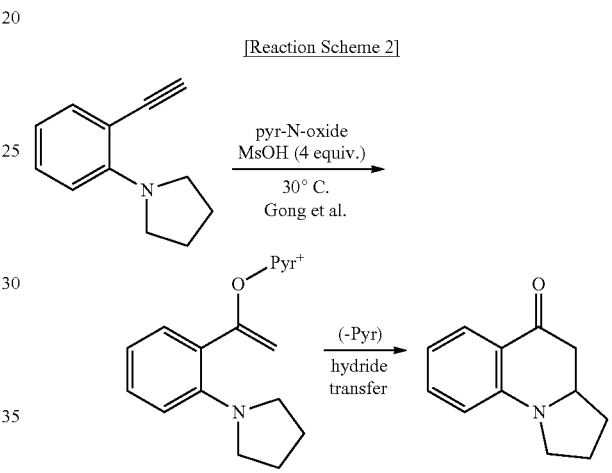

Although the above-described approach adopts a reaction of an alkyne compound without using a metal catalyst, an excess amount of acid is used or the reaction is carried out at a high temperature. Therefore, the application range of the reaction route is restricted since the applicable functional groups are limited and the reaction is implemented by only intramolecular reactions.

Accordingly, coupling methods that effectively synthesize useful compounds, such as 1,1-diaryl compounds, 1,1-diheteroaryl compounds, and 1,4-dicarbonyl compounds, and that are applied to various fields using intermediates having equivalent reactivity to carbene intermediates without using transition metals are required.

SUMMARY OF THE INVENTION

According to an aspect of the present disclosure, there is provided a method for preparing a metal-free and alkyne compound-derived reactive intermediate, which exhibits equivalent reactivity to a carbene intermediate, especially, a metal-carbene intermediate.

Another aspect of the present disclosure is to provide a method capable of preparing various compounds, such as 1,1-diaryl compounds, 1,1-diheteroaryl compounds, and 1,2-dicarbonyl compounds, under mild conditions by passing through the foregoing metal-free and alkyne compound-derived reactive intermediate and conducting an intermolecular coupling reaction of the intermediate and a wide variety of nucleophiles.

In accordance with an aspect of the present disclosure, there is provided a method for preparing an alkyne compound-derived reactive intermediate, the method including:

reacting an alkyne compound represented by General Formula 1 with a N—O bond oxidant in the presence of a Brønsted acid-containing catalyst in an organic solvent to form an alkyne-oxidant adduct:

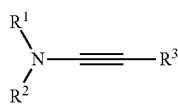

[General Formula 1]

wherein, $R^1$ is carbonyl ($R^4C(O)$), sulfonyl ($R^4SO_2$), carbamate ($R^4OC(O)$), or sulfinyl ($R^4S(O)$), as a substituent that lowers electron density of N atoms, and $R^4$ is selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having 01-C40 amine, a C3-C40 cycloalkyl group, and a heterocycloalkyl group having 3 to 40 heteronuclear atoms;

$R^2$ and $R^3$ each are independently selected from the group consisting of hydrogen, deuterium, halogen, a cyano group, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having 01-C40 amine, a C3-C40 cycloalkyl group, and a heterocycloalkyl group having 3 to 40 heteronuclear atoms, and $R^2$ and $R^3$ may bind to a neighboring group to fault a fused ring; and $R^1$ and $R^2$ may bind to each other to form an indole ring, and respective substituents at positions 2, 3, 4, 5, 6, and 7 of the indole are selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms.

In accordance with another aspect of the present invention, there is provided a method for oxygenative coupling of an alkyne compound, the method including:

reacting an alkyne compound represented by General Formula 1 with a N—O bond oxidant in the presence of a Brønsted acid-containing catalyst in an organic solvent to form an alkyne-oxidant adduct intermediate; and subsequently reacting the alkyne-oxidant adduct intermediate with a nucleophile (Nu) to form a compound represented by General Formula 2 below:

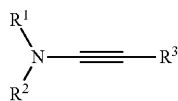

[General Formula 1]

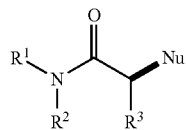

[General Formula 2]

wherein, $R^1$ is carbonyl ($R^4C(O)$), sulfonyl ($R^4SO_2$), carbamate ($R^4OC(O)$), or sulfinyl ($R^4S(O)$), as a substituent that lowers electron density of N atoms, and $R^4$ is selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms;

$R^2$ and $R^3$ each are independently selected from the group consisting of hydrogen, deuterium, halogen, a cyano group, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms, and $R^2$ and $R^3$ may bind to a neighboring group to form a fused ring;

$R^1$ and $R^2$ may bind to each other to form an indole ring, and respective substituents at positions 2, 3, 4, 5, 6, and 7 of the indole are selected from the group consisting of a 01-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms; and Nu is selected from the group consisting of a C6-C40 substituted phenol group, a C6-C40 substituted aniline group, an indole group having 8 to 40 heteronuclear atoms, a pyrrole group having 5 to 40 heteronuclear atoms, a 1,2-diazole group having 5 to 40 heteronuclear atoms, a C3-C40 silyl enol ether group, and a C3-C40 terminal vinyl group.

According to an embodiment, the Brønsted acid may exhibit acidity with an acid dissociation constant (pKa) in the range of −10 to 7 in an aqueous solution.

According to an exemplary embodiment, the Brønsted acid may be selected, according to the structure of a counter anion, from the following exemplified kinds: (i) conjugate acids of sulfonate, bis-sulfonimide, phosphate, phosphoramide, or carboxylate, for oxygen acids and nitrogen acids; (ii) conjugate acids of carbanions with aryl groups attached thereto, the aryl groups including one to three $CF_3$, $C_6F_5$, $SO_2CF_3$, $SO_2C_6F_5$ groups and three to five F atoms, for carbonic acids; and (iii) a combination thereof.

According to an exemplary embodiment, the Brønsted acid may be a super strong acid selected from the group consisting of HCl, $HBF_4$, and $HSbF_6$.

According to an embodiment, the organic solvent may be selected from the group consisting of: chlorine-based solvents including C1-C5 aliphatic hydrocarbons containing 1 to 5 chlorine atoms; solvents containing C6-C10 aromatic hydrocarbons; solvents containing C5-C10 aliphatic hydrocarbons; and solvents containing C1-C8 alcohol, amino, nitrile, and/or nitro groups.

According to exemplary embodiment, the organic solvent is a polar solvent, and may be at least one selected from the group consisting of dimethylformamide (DMF), dimethyl sulfoxide (DMSO), and dimethylacetamide (DMA).

According to exemplary embodiment, the organic solvent may be at least one selected from C1-C10 chain or cyclic ethers.

In the method according to the specific embodiments of the present disclosure, when 1,1-diaryl compounds, 1,1-diheteroaryl compounds, and the like are prepared from an alkyne compound, a Brønsted acid (or organic acid) catalyst is used to form an adduct intermediate of an alkyne compound and a N—O bond oxidant, the adduct intermediate having equivalent reactivity to the existing metal-carbene intermediate, and the reaction is allowed to pass through the adduct intermediate, instead of passing through an existing metal-carbene intermediate, so that the problem due to the use of a metal catalyst can be avoided. Furthermore, intermolecular oxygenative coupling reactions using a wide range of nucleophiles can be performed and high selectivity to target products can be achieved. Especially, the reduction of yield due to the excessive oxidation of the alkyne compound during the reaction can be suppressed as much as possible.

Therefore, the method according to the specific embodiment of the present disclosure is not only economical but can also be applied in the synthesis of organic materials in various fields of application (medicinal chemistry, agrochemicals, health functional foods, diagnoses, etc.) as well as basic research fields (biology, chemical biology, genetics, etc.).

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Figure 1:
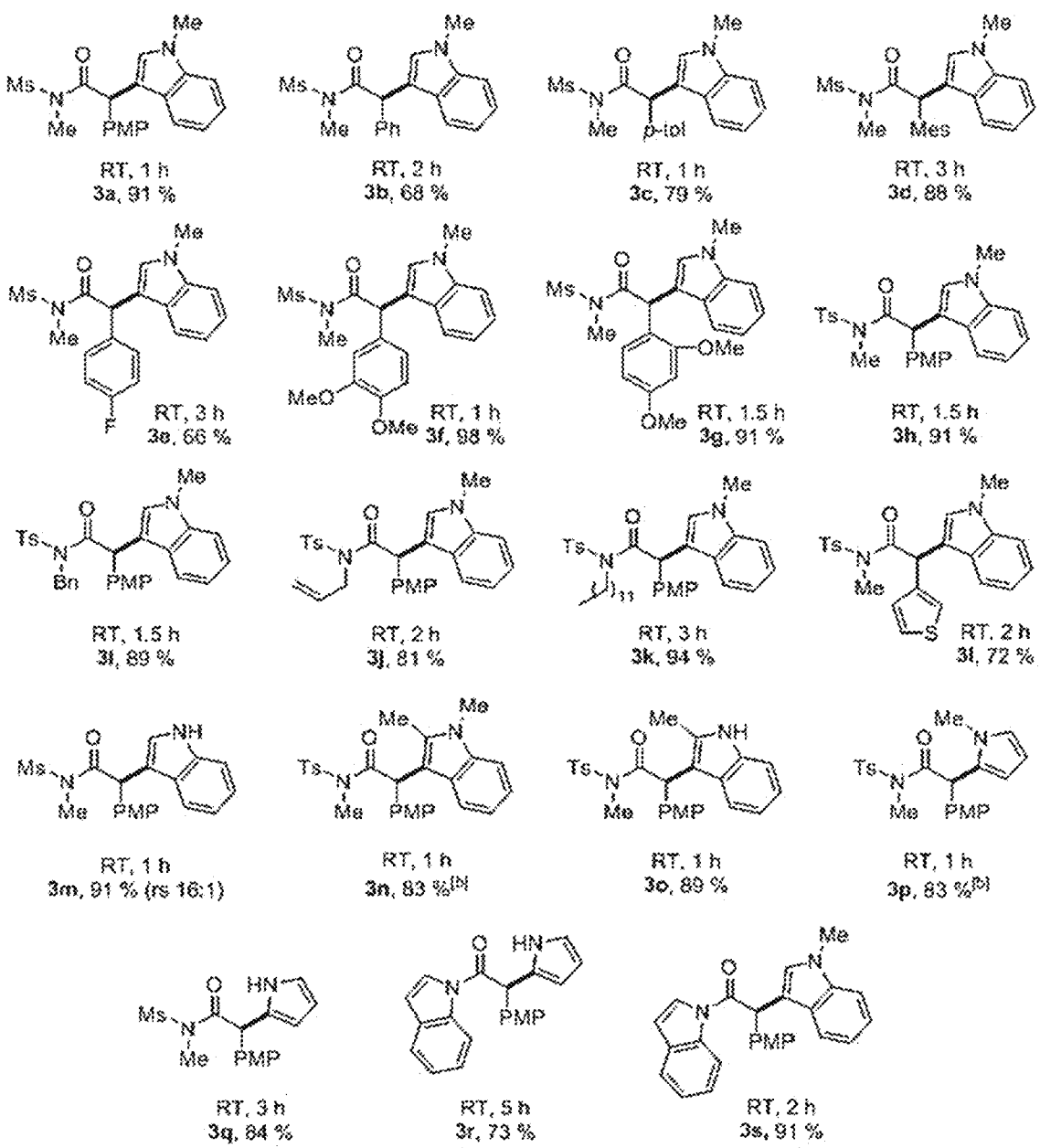
FIG. 1 shows oxygenative coupling reaction results with varying alkyne compounds when indole and pyrrole compounds were used as nucleophiles.

The present invention can be all accomplished by the following description. It is to be understood that the following description illustrates preferable embodiments of the present invention, but the present invention is not necessarily limited thereto. It is also to be understood that the accompanying drawings are included to provide a further understanding of the invention and are not intended to limit the scope of the invention.

The terms used herein may be defined as follows.

The term "adduct" may be understood to mean a chemical species formed by the addition or condensation of two or more different compounds or components.

The term "alkyl group" may mean a monovalent group derived from a straight-chain or branched-chain saturated hydrocarbon, and may be substituted or unsubstituted. Examples of the alkyl group include, but are not limited to, methyl, ethyl, propyl, isobutyl, sec-butyl, pentyl, iso-amyl, and hexyl.

The term "alkenyl group" may mean a monovalent group derived from a straight-chain or branched-chain unsaturated hydrocarbon having at least one carbon-carbon double bond, and may be substituted or unsubstituted. Examples of the alkenyl group may include, but are not limited to, vinyl, allyl, isopropenyl, and 2-butenyl.

The term "alkynyl group" may mean a monovalent group derived from a straight-chain or branched-chain unsaturated hydrocarbon having at least one carbon-carbon triple bond, and may be substituted or unsubstituted. Examples of the alkynyl group may include, but are not limited to, ethynyl and 2-propynyl.

The term "aryl group" may mean a monovalent group derived from an aromatic hydrocarbon having a single ring or a combination of two or more rings, and may be substituted or unsubstituted, and may include a simple pendent or fused form of two or more rings. Examples of the aryl group may include, but are not limited to, phenyl, naphthyl, phenanthryl, and anthryl.

The term "heteroaryl group" may mean a monovalent group derived from a monoheterocyclic or polyheterocyclic aromatic hydrocarbon, and may be one in which at least one carbon atom on a ring is substituted with a heteroatom (e.g., N, O, or S). The heteroaryl may have a simple pendant or fused form of two or more rings, and may be understood to include a fused form with an aryl group. In addition, the heteroaryl group may be substituted or unsubstituted. Examples of the heteroaryl group may include, but are not limited to: 6-membered monocyclic rings, such as pyridyl, pyrazinyl, pyrimidinyl, pyridazinyl, and triazinyl; polycyclic rings, such as phenoxathienyl, indolizinyl, indolyl, purinyl, quinolyl, benzothiazole, and carbazolyl; and 2-furanyl, N-imidazolyl, 2-isoxazolyl, 2-pyridinyl, and 2-pyrimidinyl.

The term "aryloxy group" may be a monovalent group including all —O-aryl groups and —O-heteroaryl groups, may be substituted or unsubstituted. Examples of the aryloxy group may include, but are not limited to, phenyloxy, naphthyloxy, and diphenyloxy.

The term "alkyloxy group" may mean a monovalent group having an —O-alkyl group and may be understood to include all straight-chain, branched chain, or cyclic structure, and may be substituted or unsubstituted. Examples of the alkyloxy group may include, but are not limited to, methoxy, ethoxy, n-propoxy, 1-propoxy, t-butoxy, n-butoxy, and pentoxy.

The "arylamine group" may mean an amine group substituted with aryl.

The term "cycloalkyl group" may mean a monovalent group derived from a monocyclic or polycyclic non-aromatic hydrocarbon, and may be substituted or unsubstituted. Examples of the cycloalkyl group may include, but are not limited to, cyclopropyl, cyclopentyl, cyclohexyl, and norbornyl.

The term "heterocyclic group" may mean a saturated or unsaturated group having a single ring or multiple fused rings, in which at least one carbon in a ring is substituted with a heteroatom (e. g., N, O, or S) to form a ring skeleton. The heterocyclic group may be substituted or unsubstituted, and examples thereof may include, but are not limited to, pyrrole, pyrazole, imidazole, 1,2,3-triazole, 1,2,4-triazole, and tetrazole.

The term "heterocycloalkyl group" may mean a monovalent cycloalkyl group derived from a non-aromatic hydrocarbon, in which at least one carbon atom of a ring is substituted with a heteroatom (e. g., N, O, or S). The heterocycloalkyl group may be substituted or unsubstituted, and examples thereof may include, but are not limited to, morpholine and piperazine.

The term "alkylsilyl group" may mean a silyl group substituted with alkyl.

The term "arylsilyl group" may mean a silyl group substituted with aryl.

The term "silyl enol ether" may mean a group in which oxygen at the end of an enolate is bonded to an organosilicon group.

The term "halogen" may mean at least one halogen atom or substituent, and examples thereof may include fluorine, bromine, chlorine, or iodine.

The term "dihalogen" may be two substituents, each of which is independently selected from the group consisting of fluorine, bromine, chlorine, or iodine.

According to an embodiment of the present disclosure, for the intermolecular oxygenative C—C coupling reaction of an alkyne compound and a nucleophile, a Brønsted acid-catalyzed reaction is used to induce an intermolecular Friedel-Crafts type addition reaction into an umpolung enolate formed from an alkyne compound as a substrate. For this, the strategy of passing through an adduct intermediate of an alkyne compound and a N—O bond oxidant, the adduct being formed using a Brønsted acid as a catalyst, is proposed. That is, an alkyne compound, especially, an ynamide compound may be a suitable precursor of keteniminium ions under the Brønsted acid-catalyzed reaction due to the easily polarized triple bond. Here, for the intermolecular coupling reaction, it is necessary to not only minimize side reactions, such as hydration, and over-oxidation by a N—O bond oxidant, but also to control chemoselectivity among potential nucleophile to keteniminium salts (e.g., nucleophilic arene), counter bases of acid catalysts, and solvents (e.g., halogenated solvent).

According to an embodiment of the present disclosure, the keteniminium salt is allowed to selectively pass through sequential routes of the formation of an adduct of an alkyne compound and a N—O bond oxidant and the subsequent attack by a nucleophile, and this procedure is similar to a conventional case using the reactivity of a carbene (i.e., α-oxo carbene).

Without being bound to a particular theory, such an oxygenative coupling reaction is based on the $S_N2'$ reaction mechanism in which the N—O coupling cleavage of an oxidant occurs together with the attack by a nucleophile.

The adduct is a potent electrophile, and may easily induce a Friedel-Crafts type intermolecular coupling reaction with a wide range of C-nucleophiles (e.g., indoles, pyrroles, anilines, phenols, silyl enol ethers, etc.).

In an embodiment, the alkyne compound may be an ynamide compound represented by General Formula 1 below:

[General Formula 1]

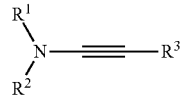

wherein, $R^1$ is carbonyl ($R^4C(O)$), sulfonyl ($R^4SO_2$), carbamate ($R^4OC(O)$), or sulfinyl ($R^4S(O)$), as a substituent that lowers electron density of N atoms, and $R^4$ is selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms;

$R^2$ and $R^3$ each are independently selected from the group consisting of hydrogen, deuterium, halogen, a cyano group, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms, and $R^2$ and $R^3$ may bind to a neighboring group to form a fused ring; and $R^1$ and $R^2$ may bind to each other to form an indole ring, and respective substituents at positions 2, 3, 4, 5, 6, and 7 of the indole are selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms.

According to a more specific embodiment, in the formula above, $R^1$ may be methylsulfonyl (Ms) or tosyl (Ts); $R^2$ may be methyl, benzyl, or allyl; and $R^3$ may be p-methoxyphenyl (PMP), 2,4,6-methyl phenyl (Mes), or 3,4-dimethoxyphenyl.

The foregoing alkyne compound may react with an oxidant having a particular bond in the presence of an acid catalyst, specifically a Brønsted acid-containing catalyst, in a solvent (specifically, an organic solvent) to form an adduct intermediate, and such an adduct intermediate may be subjected to a coupling reaction with a nucleophile (Nu) to synthesize a product represented by General Formula 2 below:

[General Formula 2]

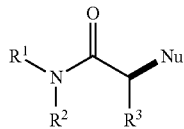

wherein $R^1$, $R^2$ and $R^3$ are as described above; and Nu may be selected from the group consisting of a C6-C40 substituted phenol group, a C6-C40 substituted aniline group, an indole group having 8 to 40 heteronuclear atoms, a pyrrole group having 5 to 40 heteronuclear atoms, a 1,2-diazole group having 5 to 40 heteronuclear atoms, a C3-C40 silyl enol ether group, and a C3-C40 terminal vinyl group.

In the above-described oxygenative coupling reaction, a kind of solvent that can act as a reaction medium of an alkyne compound and an oxidant as reactants and an acid catalyst may be used.

In this connection, a usable solvent may be selected from the group consisting of: chlorine-based solvents including C1-C5 aliphatic hydrocarbons containing 1 to 5 chlorine atoms; solvents containing C6-C10 aromatic hydrocarbons; solvents containing C5-C10 aliphatic hydrocarbons; and solvents containing C1-C8 alcohol, amino, nitrile, and/or nitro groups. These organic solvents may be used alone or in a combination of two or more thereof as a mixed solvent.

According to exemplary embodiment, the organic solvent is a polar solvent, and may be at least one selected from the group consisting of dimethylformamide (DMF), dimethyl sulfoxide (DMSO), and dimethylacetamide (DMA).

According to another exemplary embodiment, the organic solvent may be at least one selected from 01-C10 chain or cyclic ethers.

In a particular embodiment, the organic solvent may be at least one selected from the group consisting of dichloroethane, dichloromethane, chloroform (trichloromethane), chlorobenzene, 1,2-dichlorobenzene, 1,1,2,2-tetrachloroethane, 1,1,2-trichloroethane, 1,2,3-trichloropropane, 1,1,2,2-tetrachlorethylene, methanol, acetonitrile, toluene, ether, and hexane. Specifically, dichloroethane, dichloromethane, 1,2-dichlorobenzene, 1,1,2,2-tetrachloroethane, 1,1,2-trichloroethane, 1,2,3-trichloropropane, toluene, ether, hexane, or a combination thereof may be used. More specifically, dichloroethane, dichloromethane, 1,1,2-trichloroethane, or a combination thereof may be used.

According to an exemplary embodiment, the concentration of the alkyne compound in a reaction medium (organic solvent) may be in the range of, for example, about 0.05-1 M, specifically about 0.1-0.8 M, and more specifically about 0.2-0.7 M. Since excessively high or low reactant concentrations may reduce the yield of a target product (coupled reaction products), it may be advantageous to properly adjust the concentration of the reactant within the above-described range.

In an embodiment, the catalyst may be a catalyst containing a Brønsted acid. Here, the Brønsted acid may exhibit acidity with an acid dissociation constant (pKa) of, for example, about −10 to 7, specifically, −5 to 4, and more specifically, −1 to 2, in an aqueous solution.

According to an exemplary embodiment, at least one of acids exemplified as below may be used as a Brønsted acid according to the structure of a counter anion of the Brønsted acid: (i) conjugate acids of sulfonate, bis-sulfonimide, phosphate, phosphoramide, or carboxylate, for oxygen acids and nitrogen acids; (ii) conjugate acids of carboanions with aryl groups attached thereto, the aryl groups including one to three $CF_3$, $C_6F_5$, $SO_2CF_3$, $SO_2C_6F_5$ groups and three to five F atoms, for carbonic acids; and (iii) a combination thereof.

Alternatively, the Brønsted acid may be a super strong acid, and thus examples thereof may be at least one selected from the group consisting of HCl, $HBF_4$, and $HSbF_6$.

For example, $Tf_2NH$, TfOH, $HBF_4 \cdot OEt_2$, and a mixture of $HNTf_2$ and 2-Cl-pyridine may be used alone or in combination of two or more thereof as a Brønsted acid. Specifically, $Tf_2NH$, a mixture of $HNTf_2$ and 2-Cl-pyridine, TfOH, or a combination thereof may be used, and more specifically, $Tf_2NH$ and/or a mixture of $HNTf_2$ and 2-Cl-pyridine may be used.

According to an exemplary embodiment, the amount of the Brønsted acid-containing catalyst to the alkyne compound may be in the range of, for example, about 1-40 mol %, specifically about 1.5-35 mol %, and more specifically about 2-10 mol %. The amount of the catalyst in the reaction medium greatly affects the formation of the adduct and thus may be controlled within the above-described range, but is not limited thereto. The amount of the catalyst may be varied according to the alkyne compound, the N—O bond oxidant, and the like.

Meanwhile, according to a specific embodiment of the present disclosure, the N—O bond oxidant may be used as an oxidant to the alkyne compound. For example, the N—O bond oxidant may be represented by General Formula 3 or 4 below:

 [General Formula 3]

 [General Formula 4]

wherein R, R', and R" each may be a C1-C40 heteroaryl compound forming a ring together with N, and may also be a compound having axial chirality in which the rotation of a R'—R" bond is restricted according to the substituent.

According to an exemplary embodiment, the N—O bond oxidant may be represented by General Formula 5 below:

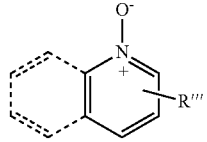 [General Formula 5]

wherein R''' is hydrogen, a halogen, a dihalogen, a cyano group, an alkoxy group, or a nitro group.

More specifically, R''' may be hydrogen, 2-chloro, 2-bromo, 2-methoxy, 4-nitro, 2,4-dichloro, 2,6-dichloro, 2,6-dibromo or 3,5-dibromo.

According to an exemplary embodiment, the foregoing oxidant represented by General Formula 3 may react with an alkyne compound of General Formula 1 in the presence of an acid catalyst to form an adduct represented by General Formula 6 below:

[General Formula 6]

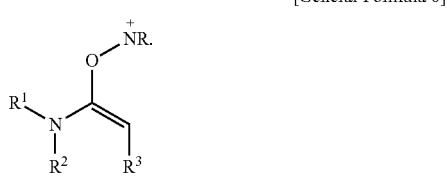

$R^1$, $R^2$, $R^3$ and R are as described above.

According to an exemplary embodiment, the N—O bond oxidant having chirality may be used to obtain a reaction product having optical activity.

Meanwhile, in an embodiment according to the present disclosure, the formation of the adduct and the coupling reaction with the nucleophile may be carried out through a single stage. For example, in cases where pyridine-N-oxide is used as a N—O bond oxidant, the oxygenative coupling reaction may be carried out through a route according to Reaction Scheme 3 below:

[Reaction Scheme 3]

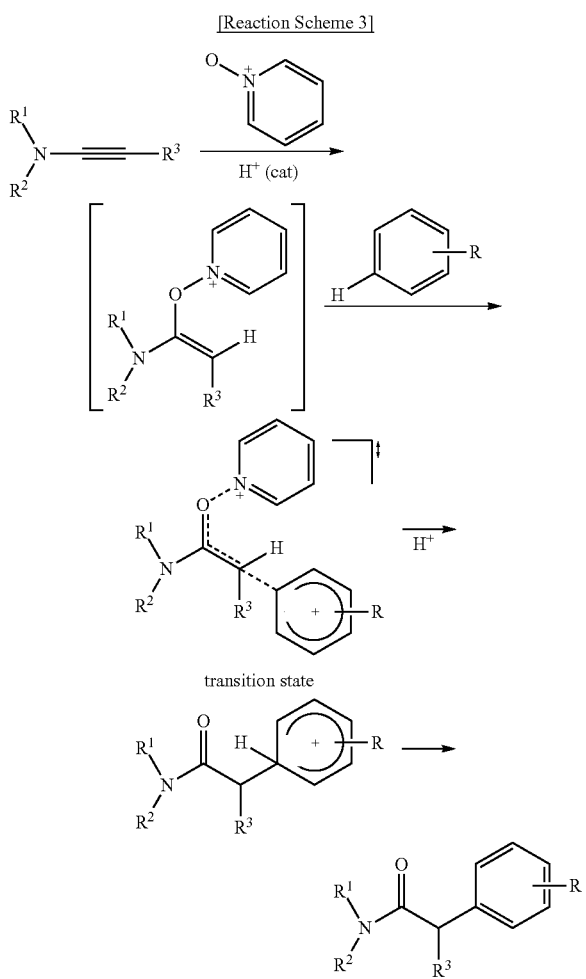

According to the reaction scheme above, during the oxygenative coupling reaction, a nucleophile and $R^3$ are bonded at the 1,1-position and a carbonyl group is formed at a neighboring position. Specifically, in the case where $R^3$ and Nu are an aryl group, 1,1-diaryl compound (specifically, 1,1-diaryl carbonyl compound) may be formed.

As described above, the nucleophile (Nu-H) used for the coupling reaction may include various indoles, pyrroles, anilines, phenols, silyl enol ethers, and the like, and may be represented by, for example, General Formulas 7 to 9 below:

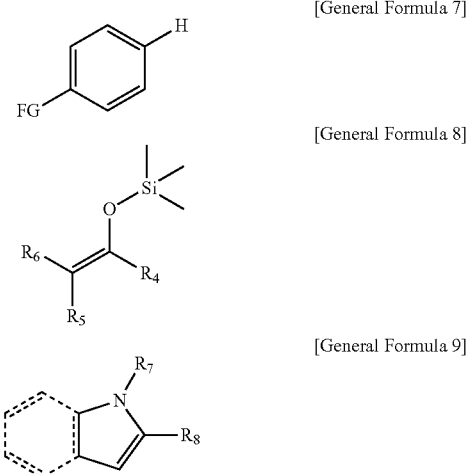

wherein FG, which is an electron donating group (EDG), is $NR_1R_2$, OH, or $OR_3$, and may be obtained by combining two or more EDGs with a benzene ring; and $R_1$ to $R_8$ each are independently selected from the group consisting of hydrogen, deuterium, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 amine, a C3-C40 cycloalkyl group, and a heterocycloalkyl group having 3 to 40 heteronuclear atoms, and $R_1$ to $R_8$ may bind to a neighboring group to form a fused ring.

In this connection, as the reaction temperature is excessively low or increased during the oxygenative coupling reaction (i.e., the formation of an adduct of an alkyne compound and a N—O bond oxidant and the coupling with a nucleophile) according to a specific embodiment of the present disclosure, the yield of a target produce decreases, and thus it is advantageous to adjust the reaction temperature to an appropriate range. According to an embodiment, the reaction temperature may be about 15-50° C., specifically about 17-40° C., and more specifically about 20-30° C., and especially room temperature. However, the temperature range is provided for the exemplary purpose, and thus the present invention is not necessarily limited to the temperature range.

It is noteworthy that the reaction can be carried out under mild reaction conditions, even at room temperature, through a catalyst reaction using a Brønsted acid. The temporal chemoselectivity can be effectively improved during the intermolecular coupling reaction through such mild reaction conditions, and thus a reaction route with high selectivity can be provided at a significantly low temperature compared with the conventional art requiring a comparatively high reaction temperature.

According to an exemplary embodiment, in cases where the amounts of the N—O bond oxidant and/or the nucleophile are excessively small or great compared with the alkyne compound as a substrate in the oxygenative coupling reaction, the yields of target products may be reduced. Therefore, according to an exemplary embodiment, the equivalent ratio of the N—O bond oxidant to the alkyne compound may be in the range of, for example, about 0.9-3, specifically about 1-2.5, and more specifically about 1.2-2.

In addition, the equivalent ratio of the nucleophile to the alkyne compound may be in the range of, for example about 1-3.5, specifically about 1.2-3.2, and more specifically about 1.5-3. However, the numerical ranges are provided for illustration, and thus the present invention is not necessarily limited thereto.

According to a specific embodiment, the equivalent ratio of alkyne compound:N—O bond oxidant:nucleophile may be in the range of, for example, 1:about 1.7-2.3:about 2.7-3.3, specifically 1 about 1.8-2.2:about 2.8-3.2, and more specifically 1:about 1.9-2.1:about 2.9-3.1.

According to an exemplary embodiment, the oxygenative coupling reaction time may be varied according to the kind of alkaline compound, the kind of oxidant, the kind of nucleophile, the concentrations of reactants, the reaction temperature, and the like. However, in the case of a highly reactive nucleophile, the oxygenative coupling reaction time on the basis of room temperature may be in the range of, for example about 15 minutes to 24 hours, specifically about 30 minutes to 18 hours, and more specifically about 1 hour to 12 hours. Alternatively, in the case of a reaction using a relatively low reactive nucleophile (e.g., a silyl enol ether), the oxygenative coupling reaction time may be described on the basis of a temperature higher than room temperature (e.g., about 80° C.), and thus the oxygenative coupling reaction time may be in the range of, for example, about 2-48 hours, specifically about 5-36 hours, and more specifically about 10-24 hours.

However, it should be noted that, as for a highly reactive nucleophile (e.g., a phenol nucleophile), the use of an existing Au catalyst requires the above-described reaction time at a high temperature (e.g., 80° C.) in order to induce an oxygenative coupling reaction, but on the reaction route according to a specific embodiment of the present disclosure, the reaction can be carried out within the above-described reaction time range even in the mild conditions, such as room temperature.

As described above, in the specific embodiment according to the present disclosure, an adduct of an alkyne compound and a N—O bond oxidant, which is formed in the presence of an acid catalyst, is used as a substitute for a carbene intermediate (i.e., α-oxo carbene) for a C—C coupling-forming intermolecular coupling reaction between an alkyne compound and a nucleophile.

As described above, the coupling reaction using an acid catalyst is performed under the mild temperature conditions, thereby increasing temporal chemoselectivity in the nucleophiles in the reaction system. Especially, a coupling reaction between two stereoselective (or enantioselective) molecules can be performed via the oxidation of the alkyne compound by using a chiral compound (e.g., chiral N,N'-dioxide) as a N—O bond oxidant.

The present invention can be more clearly understood by the following examples, and these examples are merely illustrative of the present invention and are not intended to limit the scope of the invention.

Example 1

In the present example, an oxygenative coupling reaction of an alkyne compound was carried out through two procedures below according to the nucleophile.

Materials and Measuring Devices

All solvents were dried and distilled according the standard method descried in Armarego, W. L. F.; Chai, C. L. L. Purification of Laboratory Chemicals; Elsevier: Oxford, 2009 prior to use. Pyridine-N-oxide and ynamide each were prepared according to the procedure on the literatures (Antonchick, A. P.; Org. Lett. 2015, 17, 3134 and Gillie, A. D.; Reddy, R. J.; Davies, P. W. Adv. Synth. Catal. 2016, 358, 226)

All other chemicals were purchased in the market and used as purchased.

Thin-layer chromatography (TLC) analysis was performed on the Merck silica gel 60 F254 TLC plate, and visualized using a UV lamp and a KMnO4 solution.

Flash chromatography was performed on Kieselgel 60 (230-400 mesh).

$^1$H and $^{13}$C NMR spectra were recorded on a Bruker (400 MHz) spectrometer with TMS.

High resolution mass spectrometry (HRMS) was obtained from Korea Basic Science Institute (KBSI, Daegu).

The optical purity analysis was performed on Shimadzu HPLC (LC-20A Prominence Series) using Chiralpak® IA and Chiralcel OJ-H columns (5 Um particle size, 4.6 mm×250 mm) and isopropyl alcohol and n-hexane as mobile phases.

Q-TOF mass spectrum was measured on the Agilent 6545 series Q-TOF instrument.

Experimental Procedures

A. Experimental Procedure 1 (Products 3 and 7)

The present experimental procedure was performed according to Reaction Scheme 4 below.

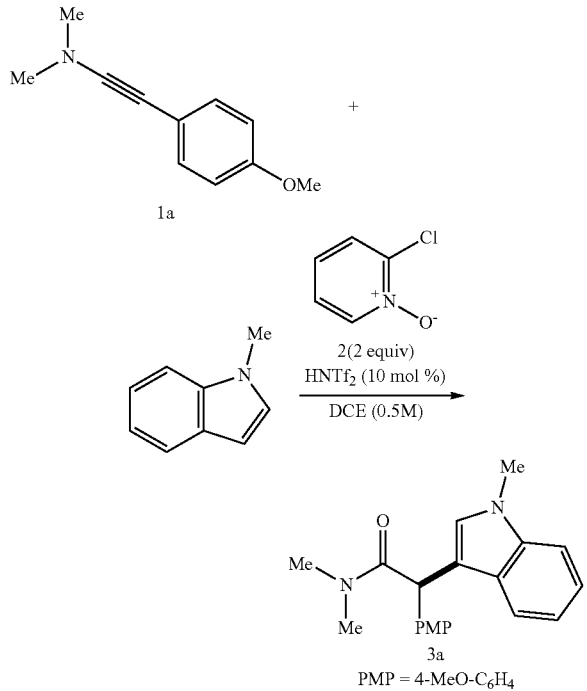

A screw cap vial was filled with a solution in which an ynamide (1a) (23.9 mg, 0.10 mmol), 2-chloropyridine N-oxide (2a) (25.9 mg, 0.20 mmol), and N-methyl indole (39.3 mg, 0.30 mmol) were dissolved in DCM (0.2 ml, 0.5 M). HNTf$_2$ (2.8 mg, 0.010 mmol) was added to the mixture, and the resulting mixture was stirred at room temperature (23° C.). Upon the completion of the reaction (determined by TLC monitoring), the crude reaction mixture was directly loaded onto a silica column, and purified by flash chromatography (eluent: hexane/ethyl acetate=2:1) to give compound 3a (35.2 mg, 91%) as a viscous oil.

B. Experimental Procedure B (Product 8)

The present experimental procedure was performed according to Reaction Scheme 5 below.

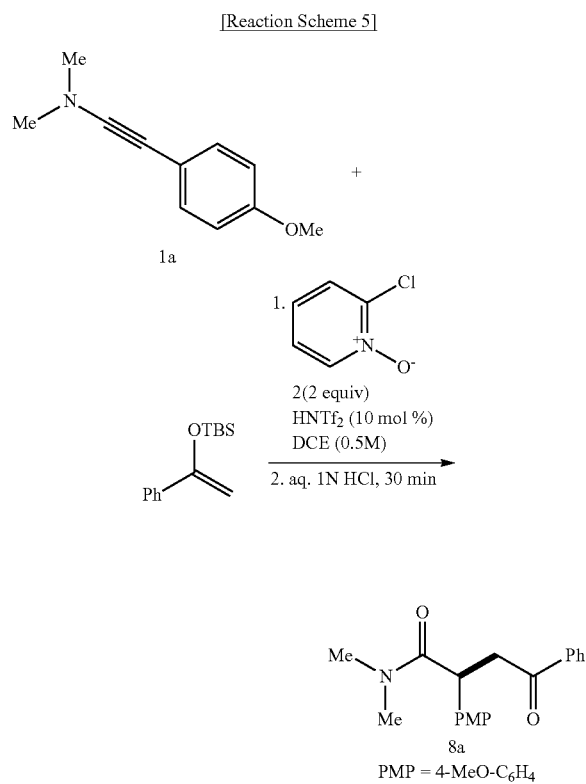

[Reaction Scheme 5]

The experimental procedure was performed in the same manner as Experimental procedure A except that the nucleophile was replaced with t-butyl dimethyl ((1-phenylvinyl)oxy)silane (70.3 mg). Upon the completion of the reaction (TLC), the crude mixture was hydrolyzed by the addition of 1N HCl (1 mL) aqueous solution, followed by vigorous stirring at room temperature for 30 minutes. The aqueous solution phase was extracted with ether (1 mL, ×3), and the combined organic phase was dried (MgSO$_4$), concentrated, and purified by flash chromatography (eluent: hexane/ethyl acetate=2:1) to give compound 8a (28.9 mg, 77%) as a viscous oil. As for compounds 8a, 8d and 8e, the diastereomeric ratio was determined from crude NMR after hydrolysis (dr 3.6/1).

Selection of Acid Catalyst

The reactions was performed according to Reaction Scheme 6 below, and the results are shown in Table 1 below.

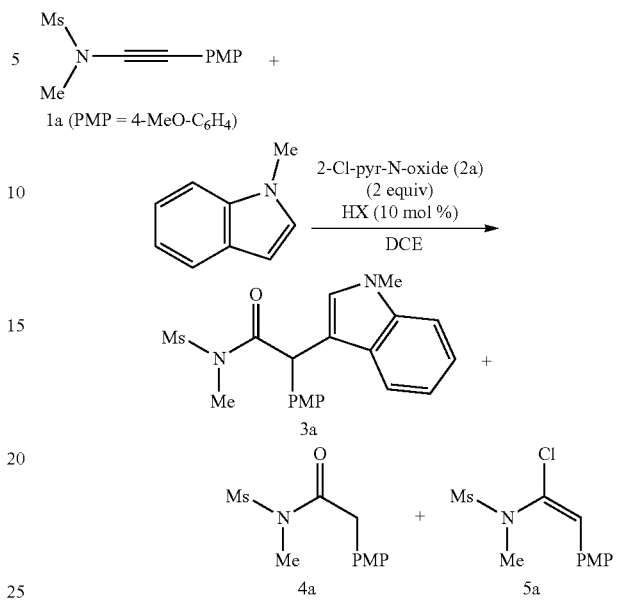

[Reaction Scheme 6]

TABLE 1

| Entry | Acid (HX) | Reaction conditions | Yield (%) (3a/4a/5a) |
|---|---|---|---|
| 1 | HCOOH | 80° C., 24 h | 0/25/20 |
| 2 | PhCO$_2$H | 80° C., 24 h | 0/17/32 |
| 3 | MsOH | 80° C., 8 h | 53/8/6 |
| 4 | TsOH•H$_2$O | 60° C., 4.5 h | 59/14/0 |
| 5 | TfOH | RT, 2 h | 76/6/0 |
| 6 | HBF$_4$•OEt$_2$ | RT, 1.5 h | 68/9/0 |
| 7 | HNTf$_2$ | RT, 25 min | 79/0/0 |
| 8[b] | HNTf$_2$ | RT, 15 min | 89/0/0 |
| 9[b, c] | HNTf$_2$, 2-Cl-pyr | RT, 15 min | 87/0/0 |
| 10[b, d] | HNTf$_2$ | RT, 12 h | 75/0/0 |

[a] Unless otherwise mentioned, an ynamide (1a) (0.1 mmol), 2-chloropyridine N-oxide (2a) (0.2 mmol), and N—Me-indole (0.3 mmol) were reacted in DCE (0.1M). The yield was measured by $^1$H NMR spectrum.
[b] 0.5M DCE was used.
[c] A mixture of HNTf$_2$ and 2-Cl-pyridine (1:1, each 10 mol %) was used as a catalyst.
[d] 2.5 mol % of HNTf$_2$ was used.

According to the table above, it was verified that HNTf$_2$ was the most suitable acid catalyst (see Entries 1-7) as a result of testing various Brønsted acids. Weak acids required a higher temperature and longer reaction time in the conversion reaction, and induced a hydration reaction (4a) as a competitive reaction. In the case where the concentration was increased, the reaction time was further reduced, and thus a yield of 89% was obtained in 15 minutes at room temperature (Entry 8).

Actually, the use of 2-Cl-pyridinium NTf$_2$ salt (10 mol %) was effective for all the cases (Entry 8 and entry 9 on Table 1). In addition, a lowered amount of the acid catalyst (2.5 mol %) took 12 hours at room temperature until the reaction was completed, but the yield of compound 3a was 75%, which was still high.

It can be seen from the above-described experimental results that the optimized conditions in the present disclosure are milder than a gold-catalyzed reaction or conventional acid-mediated conditions (typically, high-temperature conditions of about 80° C.) and/or a stoichiometric amount of acid. As a result, excessive oxidation or hydration, which often occurs at a higher temperature, was not observed.

Selection of Oxidant

Since the reaction efficiency is highly dependent on the structure of a pyridine-N-oxide oxidant, the reaction was carried out according to Reaction Scheme 7 below with different kinds of oxidants for the selection of a suitable oxidant. The results are shown in Table 2 below.

[Reaction Scheme 7]

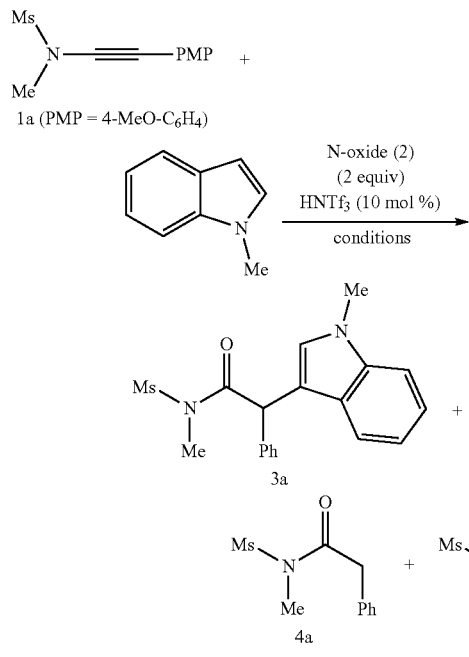

Here, the N—O bond oxidants are shown in General Formula 10 below.

[General Formula 10]

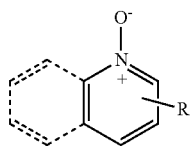

2a R = 2-Cl
2b R = 2-CN
2c R = 2,6-Br$_2$
2d R = 2,6-Cl$_2$
2e R = 2-Me
2f 8-methyl quinoline

TABLE 2

| Entry | N—O oxidant | Reaction conditions | Yield (%) (3b/4b/5b) |
|---|---|---|---|
| 1 | 2a | RT, 15 min | 89/0/0 |
| 2 | 2b | RT, 30 min | 80/0/0 |
| 3 | 2c | RT, 30 min | 77/0/0 |
| 4 | 2d | RT, 30 min | 70/0/0 |
| 5 | 2e | 80☐, 4 h | 58/0/0 |
| 6 | 2f | 60☐, 3 h | 75/0/0 |

[a] An ynamide (1a) (0.1 mmol), N-oxide (2) (0.2 mmol), and N—Me-indole (0.3 mmol) were reacted in DCE (0.5M). The yield was measured by $^1$H NMR spectrum.

According to the table above, considering that one equivalent of pyridine released in the mixture buffered an acid catalyst, a lower basic pyridine (pKa=0.49 for 2-Cl-pyridinium salt) was important.

Evaluation of Reaction Characteristics According to Alkyne Compound

In cases where indoles and pyrroles were used as nucleophiles under the optimized reaction conditions as described above, reaction characteristics with varying alkyne compounds were evaluated. For this, the reaction[a] was carried out according to Reaction Scheme 8 below using various indoles and pyrroles as nucleophiles, and the results are shown in FIG. 1 ([a]: Unless otherwise mentioned, an ynamide (1) (0.1 mmol), 2-chloropyridine N-oxide (2a) (0.2 mmol), and indole/pyrrole (0.3 mmol) were reacted in the presence of HNTf$_2$ (10 mol %) in DCE (0.5 M): The isolated yield was obtained after chromatography; PMP(p-MeO—C$_6$H$_4$), Mes(2,4,6-Me$_3$-C$_6$H$_2$); [b] 1.5 eq. of 1,2-dimethyl indole was used).

[Reaction Scheme 8]

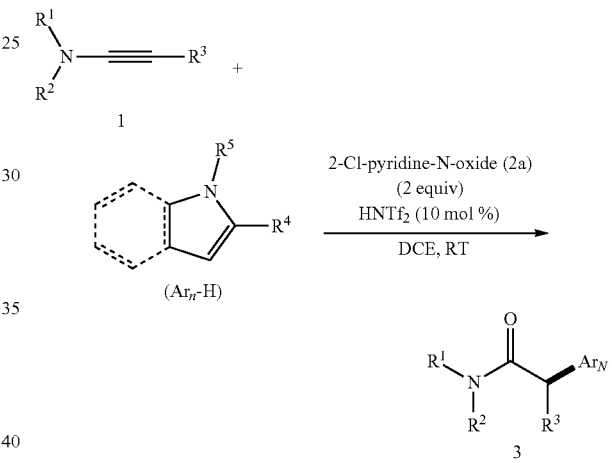

A series of ynamide substrates were effectively subjected to a coupling reaction to produce corresponding 1,1-diarylamide compounds (3). The reaction was somewhat sensitive to electronic characteristics of the Ar group at R$^3$, but showed reasonable product yields (3b to 3g). It is noteworthy that even in cases of bulky aryl groups, excellent yields of products (3d and 3g) were obtained without delaying the reaction.

It was verified that all the ynamides having Bn (3i), N-allyl (3j), and alkyl (3k) at R$^2$ and ynamides having 3-thienyl (3l) at R$^3$ (pharmaceutically important) were suitable substrates. In addition, pyrroles (3p, 3q, and 3r), N-unsubstituted indoles (3m and 3o) and 1,2-dimethylindole (3n) were also successfully converted at room temperature, and could be synthesized at high yields (or high yields and selectivity) for a short time. Here, it is interesting that ynamides (3r and 3s) are excellent substrates.

Meanwhile, for the product (3n), the use of 3 eq. of the nucleophile resulted in the direct formation of a significant amount of arylation products, thereby reducing the amount of the nucleophile, thus increasing the yield.

Evaluation of Effects of Nucleophiles

Figure 2:
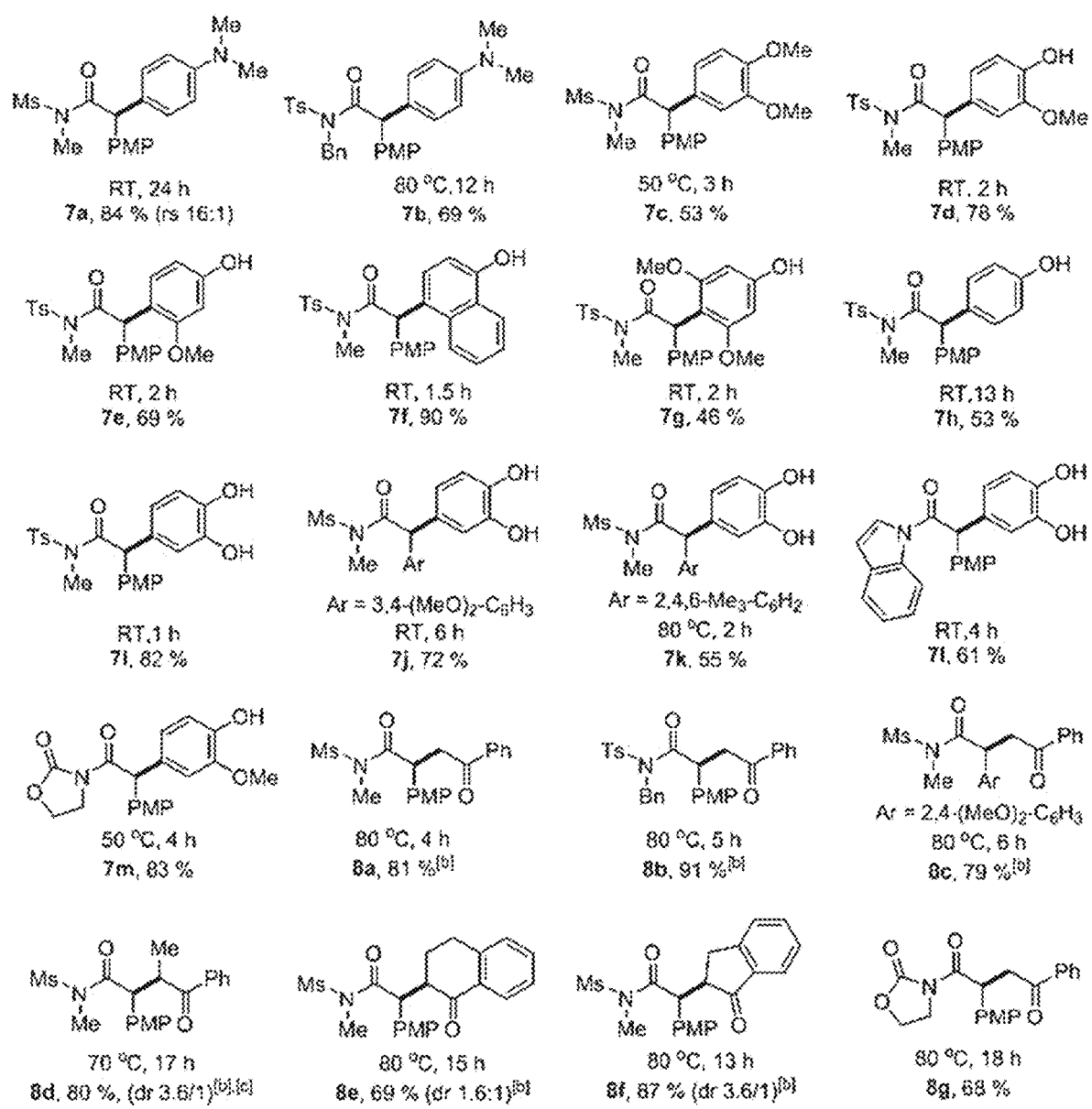
FIG. 2 shows oxygenative coupling reaction results when various arenes, phenols, and silyl enol ethers were used as nucleophiles.

Based on the successful coupling reaction with indoles and pyrroles, it was evaluated whether the oxygenative alkyne-arene coupling reaction was also applicable to a relatively less nucleophilic arene. For this, the reaction was carried out according to Reaction Scheme 9 below using an arene, a phenol, and a silyl enol ether as nucleophiles, and the results are shown in FIG. 2. ([a]: an ynamide (1) (0.1 mmol), 2-Cl-pyridine-N-oxide (2a) (0.2 Hanoi), and arene/phenol/silyl enol ether (0.3 mmol) were reacted in the presence of HNTf$_2$ (10 mol %) in DCE (0.5 M): The isolated yield was obtained after chromatography; [b] Crude products were hydrolyzed with a 1 N hydrochloric acid aqueous solution prior to purification; and [c] (Z)-silyl enol ether was used).

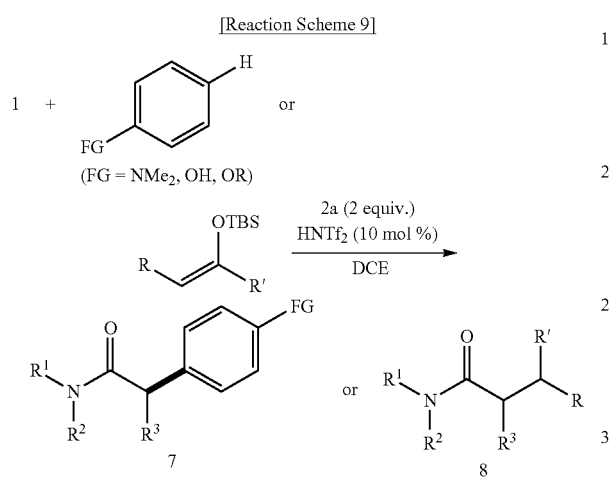

[Reaction Scheme 9]

As a result of the Friedel-Crafts type alkylation of N,N-dimethyl aniline as a nucleophile, the products (7a to 7b) were produced with favorable yields and positional selectivity. However, the reaction rate was slow for a relatively less nucleophilic alkoxy arene (7c).

In addition, a favorable coupling reaction was achieved for the phenol. In the cases where o- or m-guaiacol (7d, 7e), 1-naphthol (7f), phenol (7h), catechols (7i to 7l) and even sterically demanding phenol (7g) were used, the respective coupled products could be obtained efficiently as single regioisomers.

Subsequently, it was examined whether such approach could also be applied to the preparation of 1,4-dicarbonyl compounds. With silyl enol ether as a nucleophile, 1,4-dicarbonyl compounds (8a to 8f) were obtained after hydrolysis. For 2-substituted silyl enol ethers (8d to 8f), the products were obtained as a mixture of diastereomers (dr 3.6/1 to 1.6/1).

Example 2

Identification of Reaction Mechanism

Figure 3:
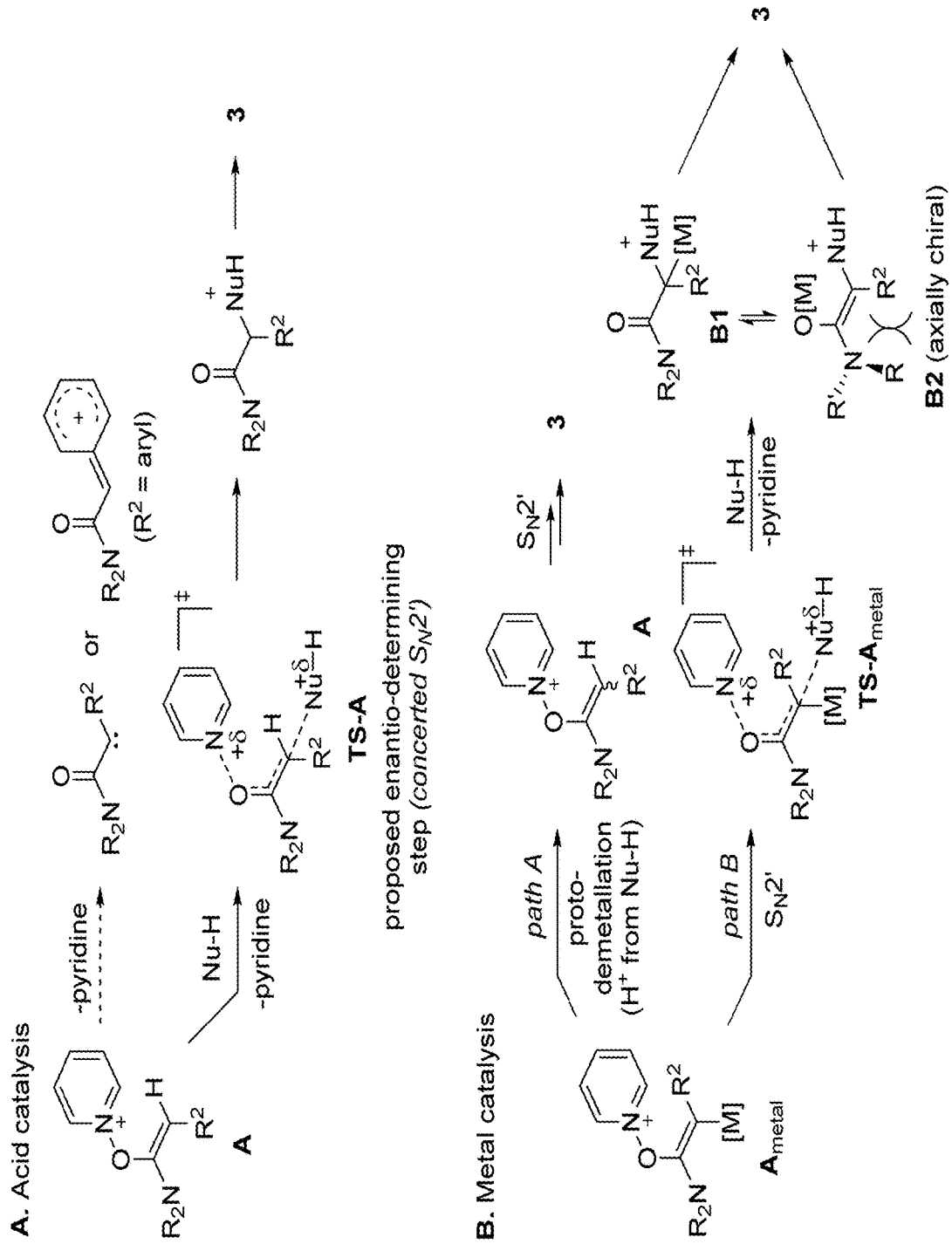
FIG. 3 shows possible reaction routes in carrying out an acid-catalyzed reaction and a metal-catalyzed reaction from intermediates.

A mechanism by which an alkyne compound is oxidized by pyridine-N-oxide through a Brønsted acid-catalyzed reaction was identified. In this connection, possible reaction routes in carrying out an acid-catalyzed reaction and a metal-catalyzed reaction from an intermediate are shown in FIG. 3.

According to the previous studies, it has been known that, under the Brønsted acid or Lewis acid conditions, the ynamide/pyridine-N-oxide adduct (A) passed through a carbene route (based on the 1,2-hydride shift), a phenylium ion, or a concerted S$_N$2' route during the N—O coupling redox reaction. The former two reaction routes are distinguished from the other route in that the N—O bond cleavage occurs prior to the attack by an arene. Therefore, when the enantio-induction using chiral pyridine-N-oxide was observed, such a product may serve as a test for the concerted S$_N$2' mechanism.

An oxidation conversion reaction was carried out using the chiral bipyridine-N,N'-dioxide of Nakajima as shown in Reaction Scheme 10 below.

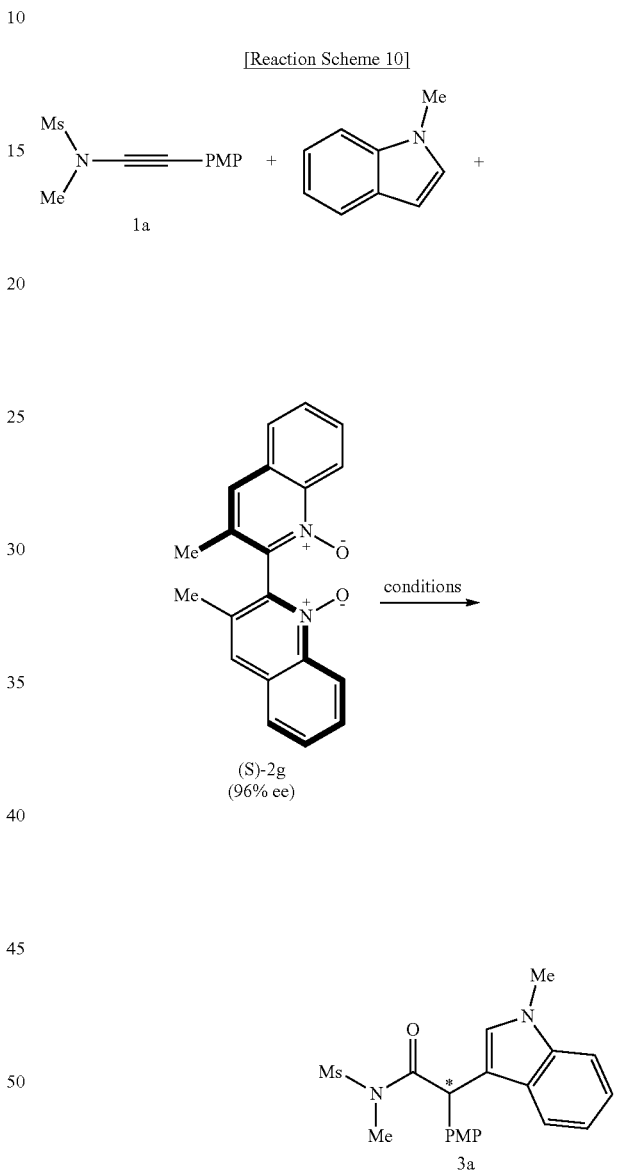

[Reaction Scheme 10]

| conditions | |
|---|---|
| HNTf$_2$ (10 mol %), DCE, rt, 2 h | 94% (83% ee) |
| iPrAuNTf$_2$ (5 mol %), DCE, rt, 45 h | 84% (82% ee) |
| iPrAuNTf$_2$ (5 mol %), water, 80° C., 2 h | 76% (71% ee) |
| Zn(OTf)$_2$ (5 mol %), DCE, 80° C., 1 h | 92% (66% ee) |

First, according to a known procedure, chiral pyridine-N—N' dioxide (S)-2g was prepared by using (R,R)-dibenzoyl-L-tartaric acid as a chiral decomposing agent and employing the chromatographic separation of diastereoisomeric salts as shown in Reaction Scheme 11 below (Nakajima, M.; Shiro, M.; Hashimoto, S. Tetrahedron: Asymmetry 1997, 8, 341).

[Reaction Scheme 11]

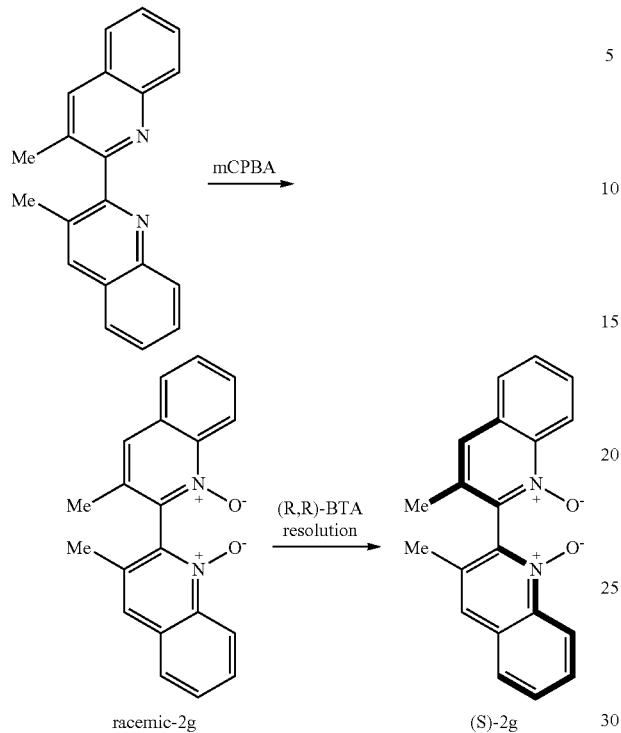

Figure 4A:
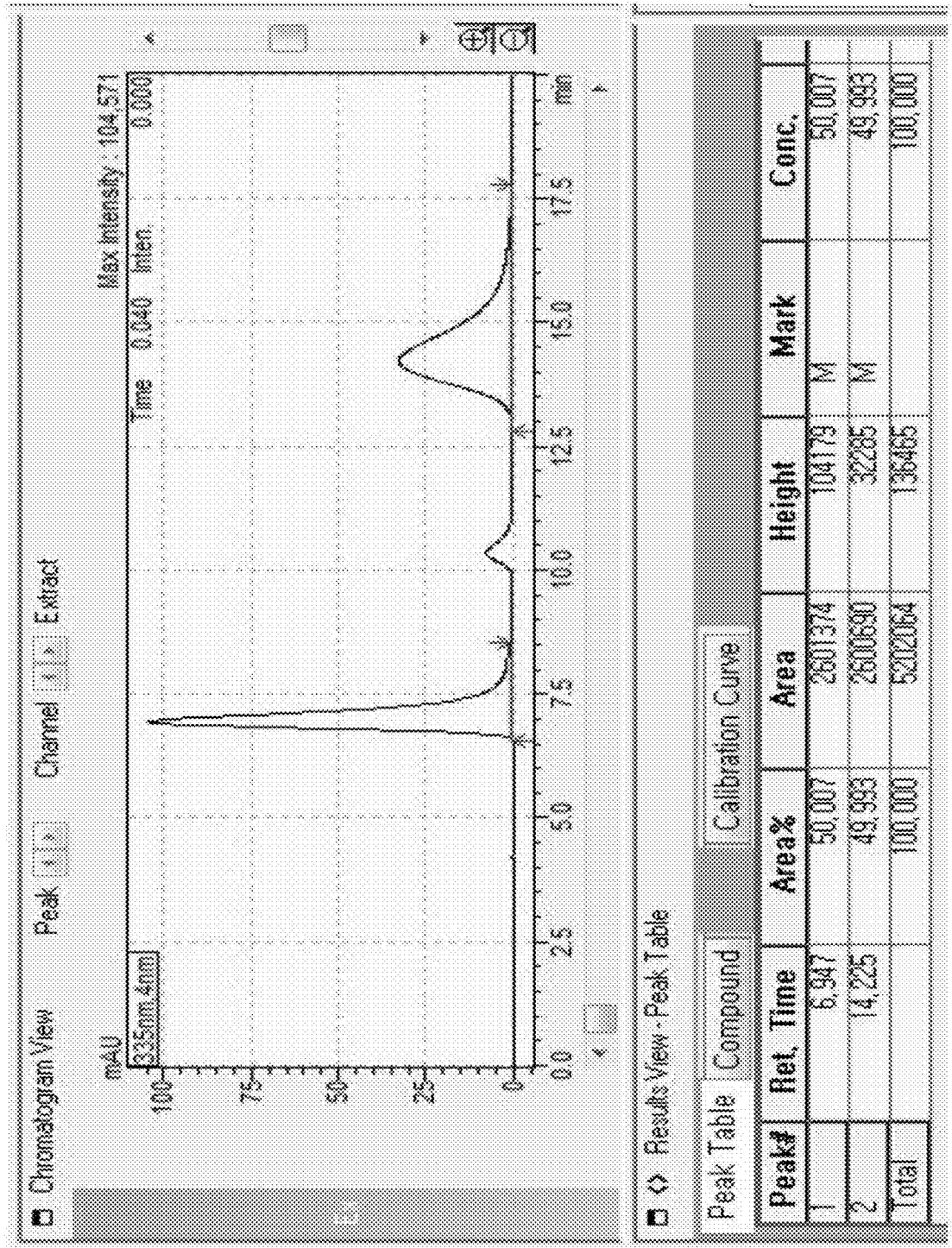
FIGS. 4a and 4b show HPLC chromatograms of racemic-pyridine-N—N' dioxide (2g) and chiral pyridine-N—N' dioxide-(S)-2g), respectively.
Figure 4B:
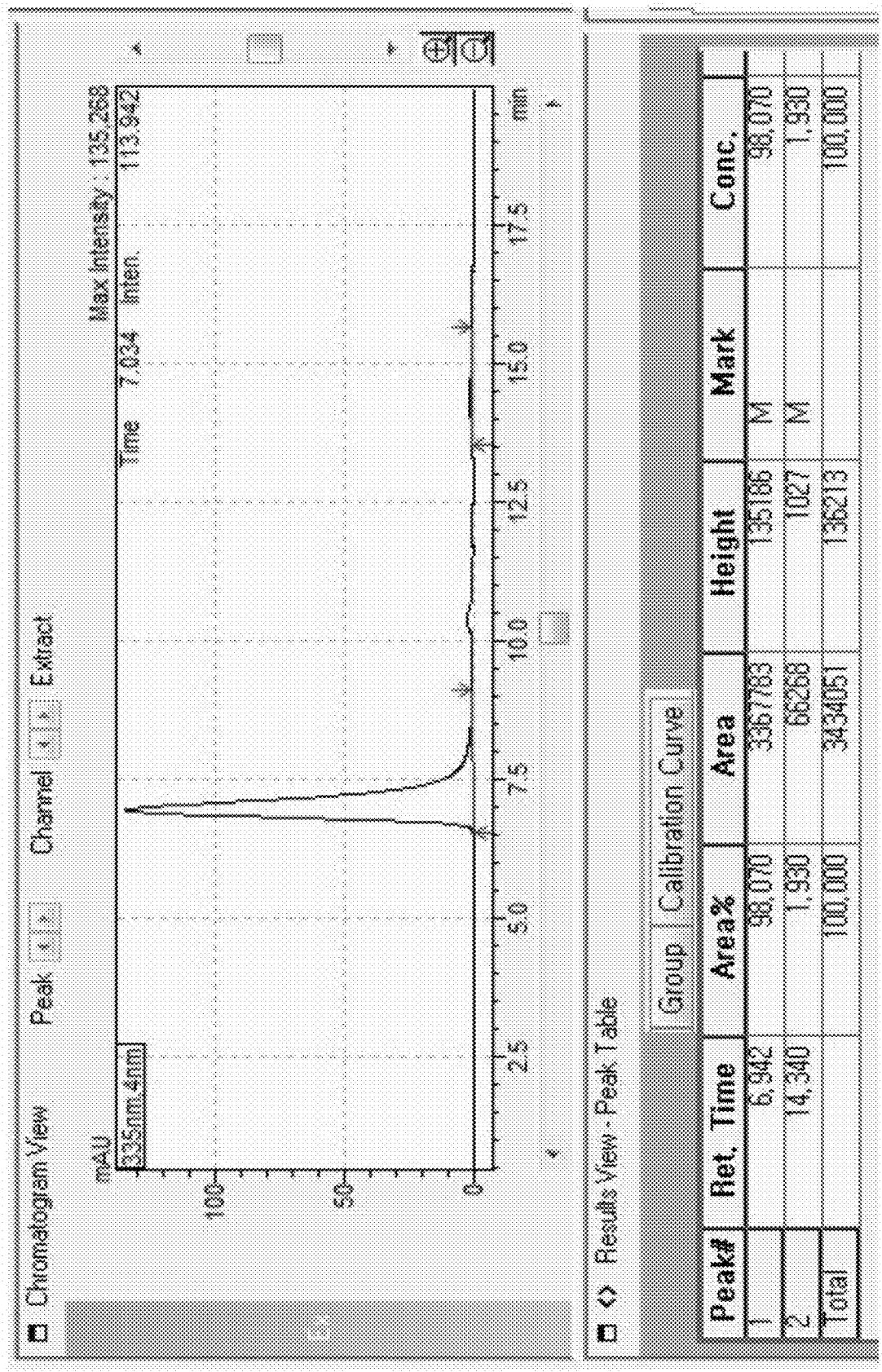

HPLC chromatograms of racemic-2g and (S)-2g are shown in FIGS. 4A and 4B. The optical purity (enantiopurity) was determined by chiral HPLC analysis ((96% ee, Chiralcel OJ-H, n-hexane/iPrOH=2:1); [a] D-122 (c=1.0, CHCl$_3$)).

A. Preparation of Racemic Sample (3a)

Figure 5A:
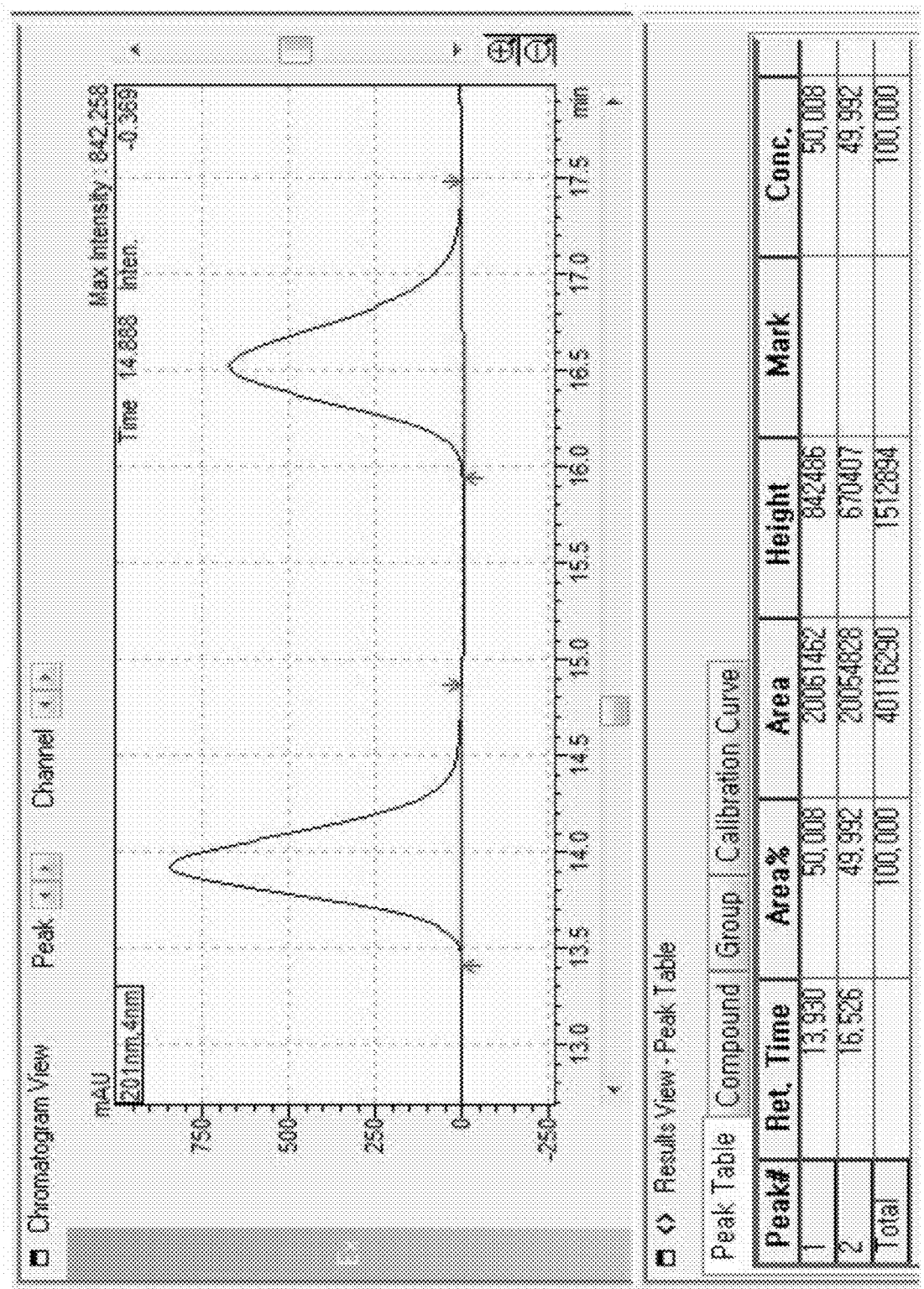
FIGS. 5a and 5b show HPLC analysis results of a racemic sample (3a) and a sample (3a) obtained using a chiral oxidant (2g), respectively.

A racemic sample was prepared according to Experimental Procedure 1. Chiral analysis was performed on the Chiralpak® IC column using IPA:n-hexane (40:60) as eluent (1 mL/min). The results are shown in FIG. 5a.

B. Preparation of Product (3a) by BrøNsted-Acid Catalyzed Reaction Using Chiral Oxidant (2g)

Figure 5B:
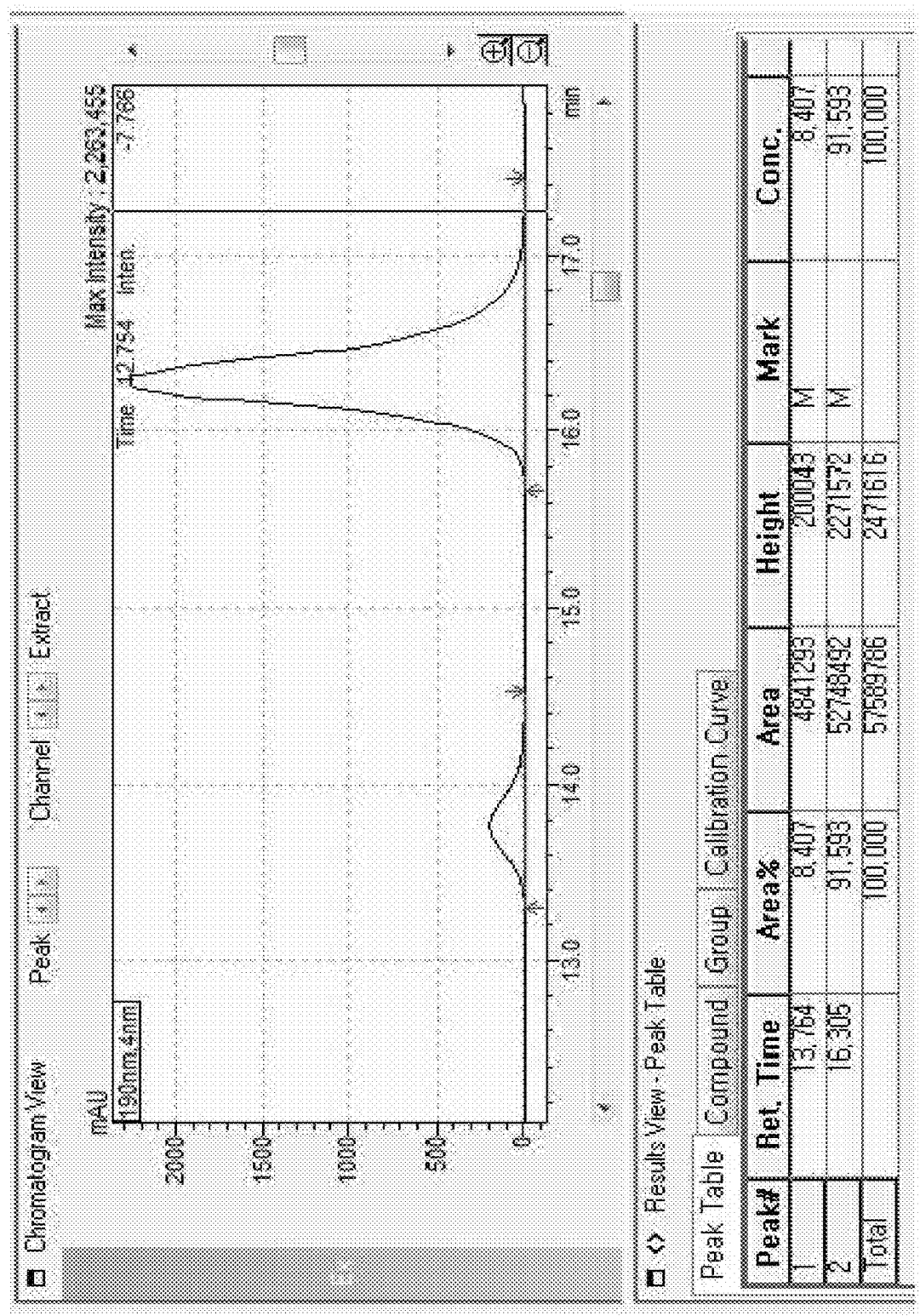

A sample was prepared according to Experimental Procedure 1, and 2-Cl-pyridine-N-oxide (2a) was substituted with a chiral oxidant (2g; 2 eq., 200 mol %). The reaction was carried out at 23° C. for 2 hours, and the separation by chromatography gave a yield of 94%. Chiral HPLC analysis was performed using the Chiralpak® IC column (83.2% ee). The results are shown in FIG. 5b. The mono-N-oxide (2g') (38%) was recovered together with unreacted N—N'-dioxide (2g; 104%), and was determined to have 6.2% ee using the chiral decomposition method by Kim et al (J. Am. Chem. Soc. 2015, 137, 14190).

However, the use of mono-N-oxide (2g') instead of di-N-oxide (2g) as an oxidant resulted in a very slow conversion reaction even though the other conditions are the same, and 52% of the product (3a) was formed at room temperature after 24 hours.

According to the above-described experimental results, when the ynamide (1a) was reacted with the stereo-rich compound (s)-2g (200 mol %) in the presence of the HNTf$_2$ catalyst, the product (3a) could be separated with a high yield (94%) and favorable stereoselectivity (83% ee), which directly supports that the reaction proceeded through the concerted S$_N$2' route. Particularly, the foregoing experiment is significant in that the experimental results first reported a stereoselective intermolecular coupling reaction through alkyne oxidation.

Comparative Examples 1 to 3

A product (3a) was prepared under the gold (Au) and zinc (Zn)-catalyzed reaction conditions through the reaction route shown in Reaction Scheme 10.

Comparative Example 1

Reaction Using IPrAuNTf$_2$ at Room Temperature

The reaction was carried out in the presence of IPrAuNTf$_2$ as a gold catalyst according to Reaction Scheme 12 below.

[Reaction Scheme 12]

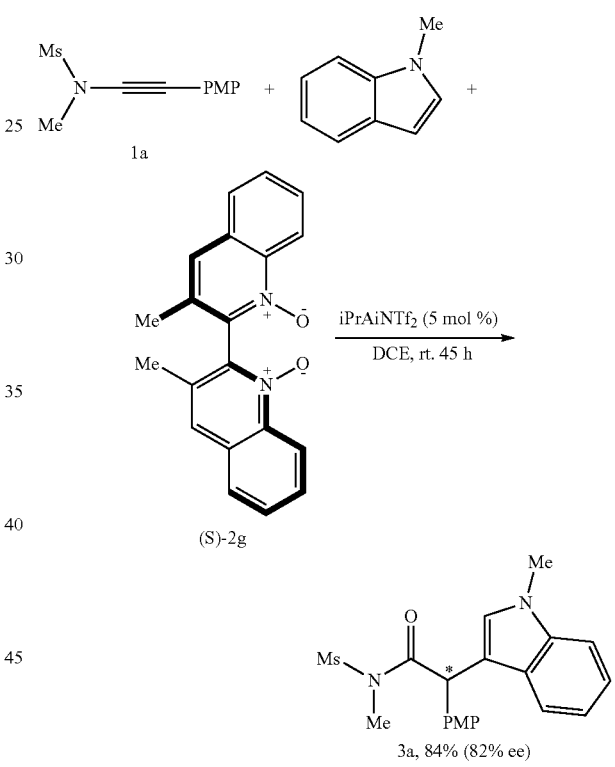

Figure 6A:
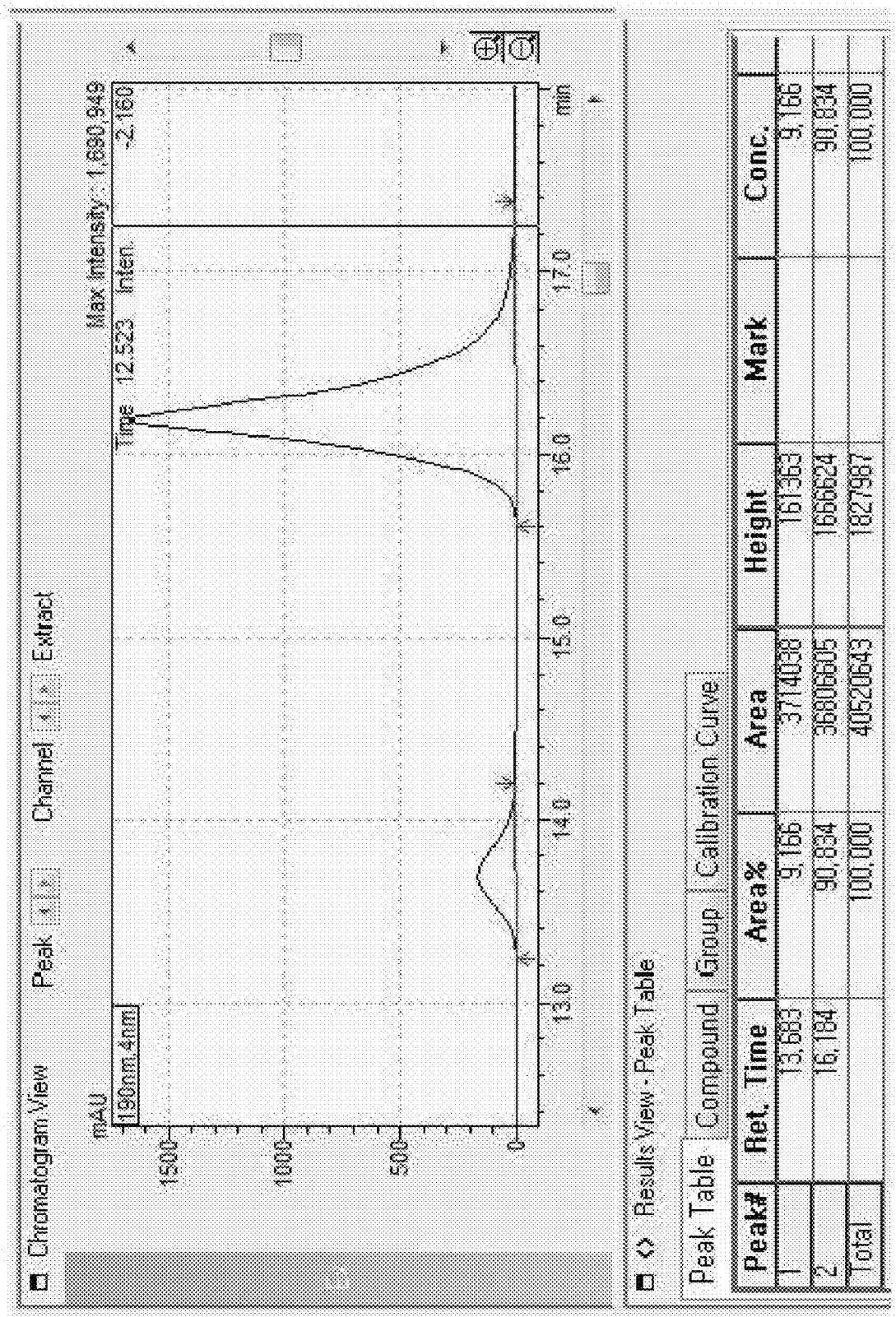
FIGS. 6a to 6c show chiral HPLC analysis results of products (3a) obtained in Comparative Examples 1 to 3, respectively.

The reaction was carried out according to Experimental Procedure 1 except that 2-Cl-pyridine-N-oxide (2a) was replaced with an oxidant (2g; 2 eq., 200 mol %) and 10 mol % of HNTf$_2$ was substituted with 5 mol % of IPrAuNTf$_2$. The reaction was carried out at 23° C. for 45 hours, and the separation by chromatography gave a yield of 84%. Chiral HPLC analysis was performed using the Chiralpak® IC column (81.7% ee). The results are shown in FIG. 6a.

Comparative Example 2

Reaction Under Conditions of Aqueous Solution Medium, Reaction Temperature of 80° C., and IPrAuNTf$_2$ Catalyst The reaction was carried out in the presence of IPrAuNTf$_2$ as a gold catalyst according to Reaction Scheme 13 below.

[Reaction Scheme 13]

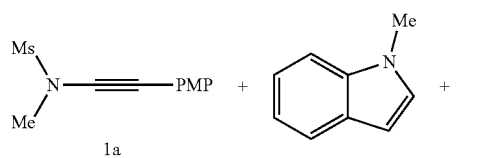

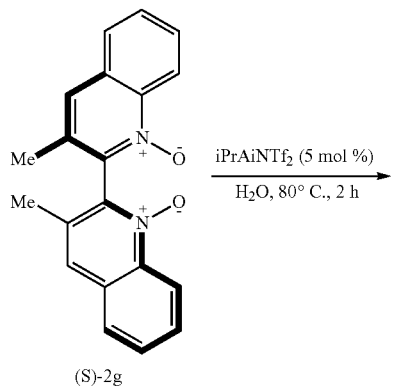

(S)-2g

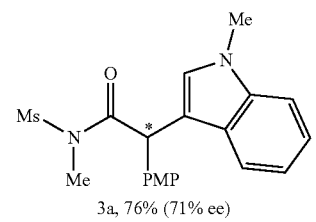

3a, 76% (71% ee)

Figure 6B:
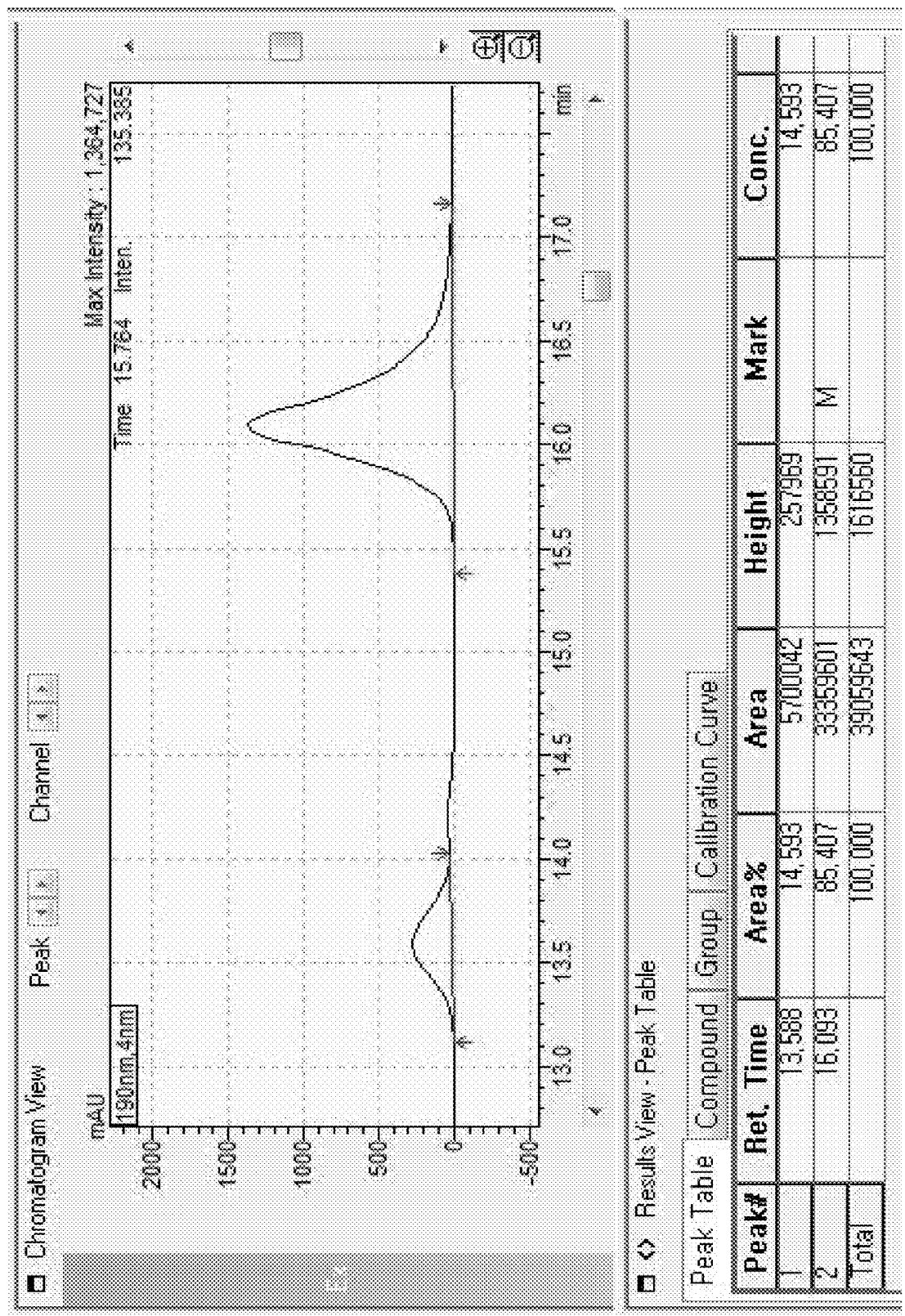

A product (3a) was synthesized by the same method as in Comparative Example 1 except that water (0.5 M) was used as the solvent and the reaction temperature was set to 80° C. The reaction was carried out for 45 hours, and the separation by chromatography gave a yield of 76%. Chiral HPLC analysis was performed using the Chiralpak® IC column (70.8% ee). The results are shown in FIG. 6b.

Comparative Example 3

Reaction in Presence of Zinc (Zn) Catalyst Using Oxidant (2g) at 80° C.

The reaction was carried out in the presence of Zn(OTf)$_2$ as a zinc catalyst according to Reaction Scheme 14 below.

[Reaction Scheme 14]

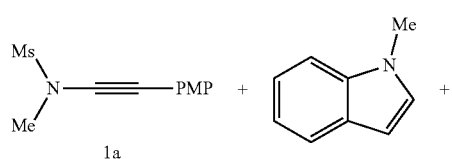

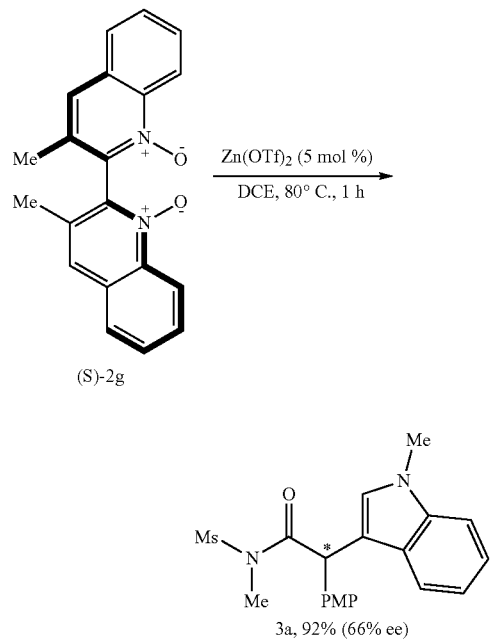

(S)-2g

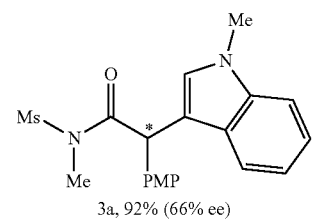

3a, 92% (66% ee)

Figure 6C:
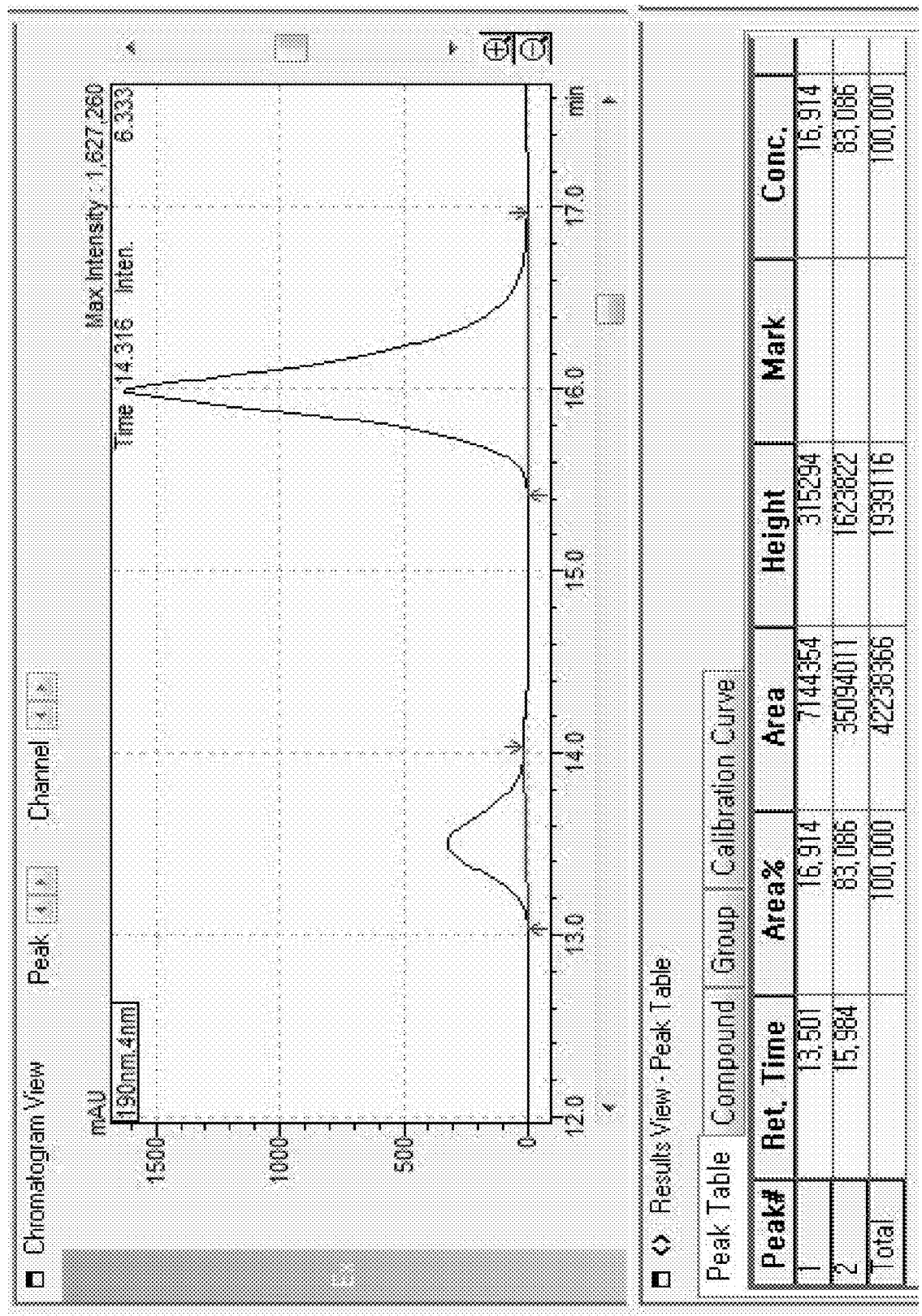

The reaction was carried out according to Experimental Procedure 1 except that 2-Cl-pyridine-N-oxide (2a) was replaced with an oxidant (2g; 2 eq., 200 mol %) and 10 mol % of HNTf$_2$ was substituted with 5 mol % of Zn(OTf)$_2$. The reaction was carried out at 80° C. for 1 hour, and the separation by chromatography gave a yield of 92%. Chiral HPLC analysis was performed using the Chiralpak® IC column (66.2% ee). The results are shown in FIG. 6c Example 3

The reaction was carried out according to Reaction Scheme 15 below.

[Reaction Scheme 15]

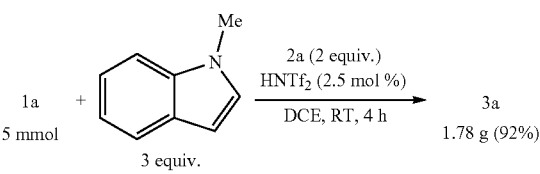

The reaction was carried out according to Example 2 except that 2.5 mol % of HNTf$_2$ was used as an acid catalyst. As a result, a high yield of about 92% was obtained, which indicates that the product (3a) could be effectively synthesized on a gram-scale.

According to Comparative Examples 1 to 3, it can be seen that the metal catalyst can also achieve the enantio-induction at a significant level of about 66-82% ee. Referring to FIG. 3, the metal-adduct (A$_{metal}$) may pass through a stereogenic SN2' addition (route A) after the conversion into A by photo-demetallation. Alternatively, the S$_N$2' route may occur on A$_{metal}$, and then the non-racemized photo-demetallation from C- or O-linked enolate B1/B2 may occur (Route B).

Example 4

Confirmation of Presence of Ynamide/N-Oxide Adduct

In the present example, it was examined whether the reaction of an alkyne compound (ynamide) and a N—O bond oxidant in the presence of an acid catalyst resulted in the formation of an ynamide/N-oxide adduct. For this, the reaction was carried out according to Reaction Scheme 16 below.

[Reaction Scheme 16]

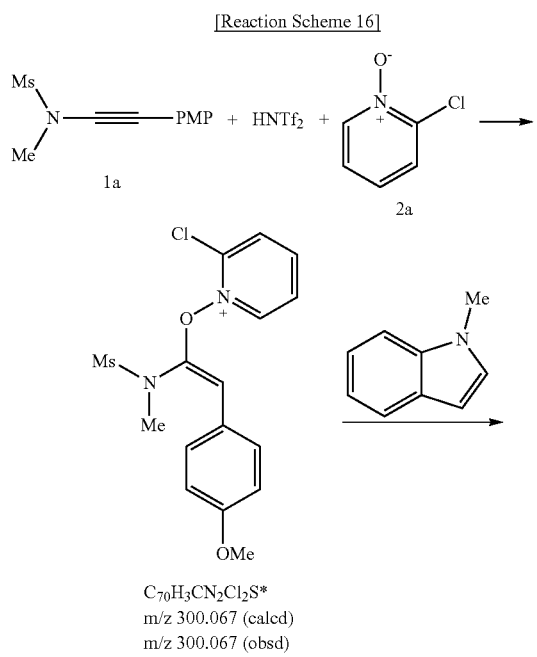

Figure 7A:
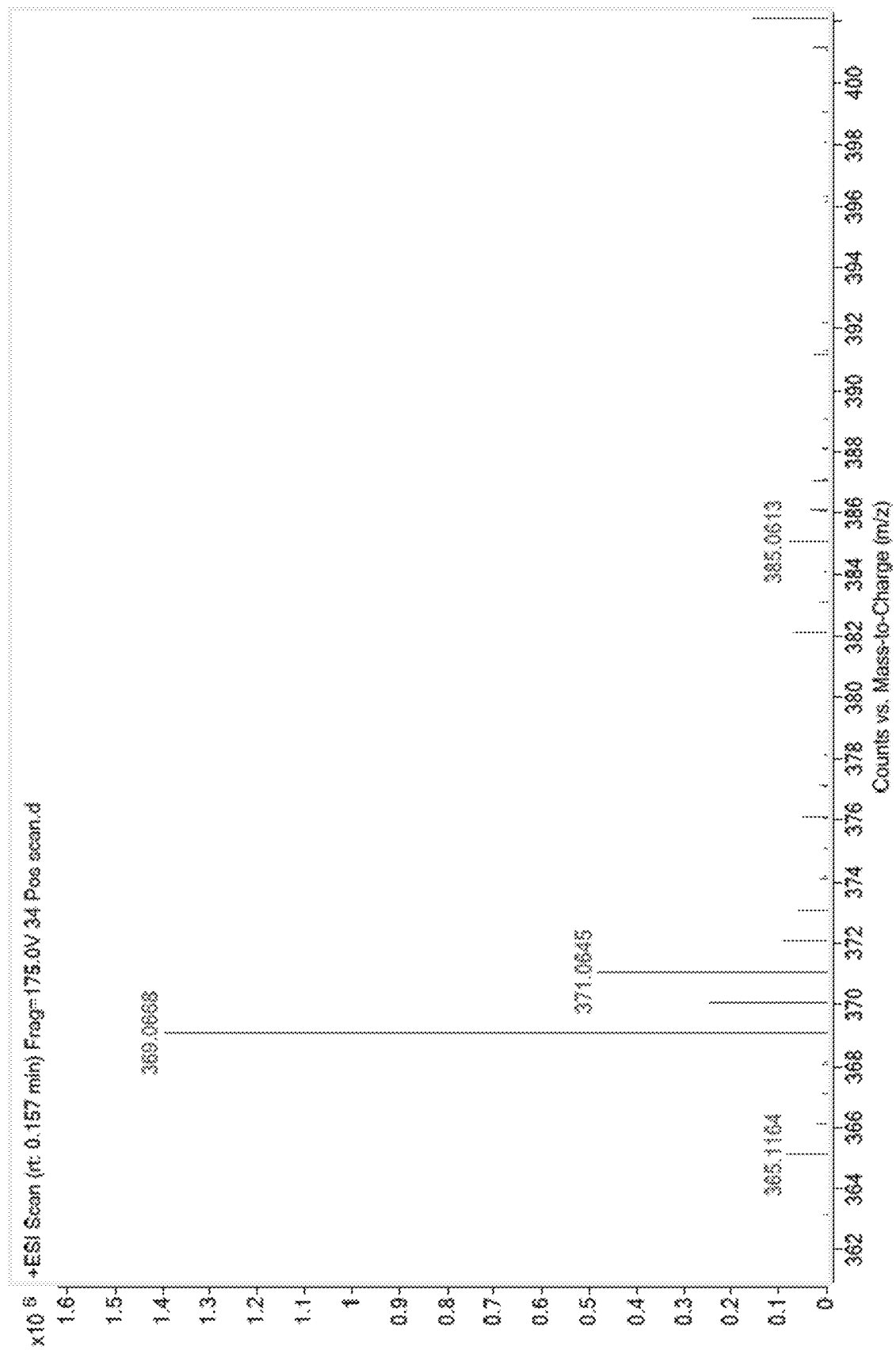
FIGS. 7a, 7b, and 7c show Q-TOF MS analysis results for examining the presence or absence of adducts in Example 4.
Figure 7B:
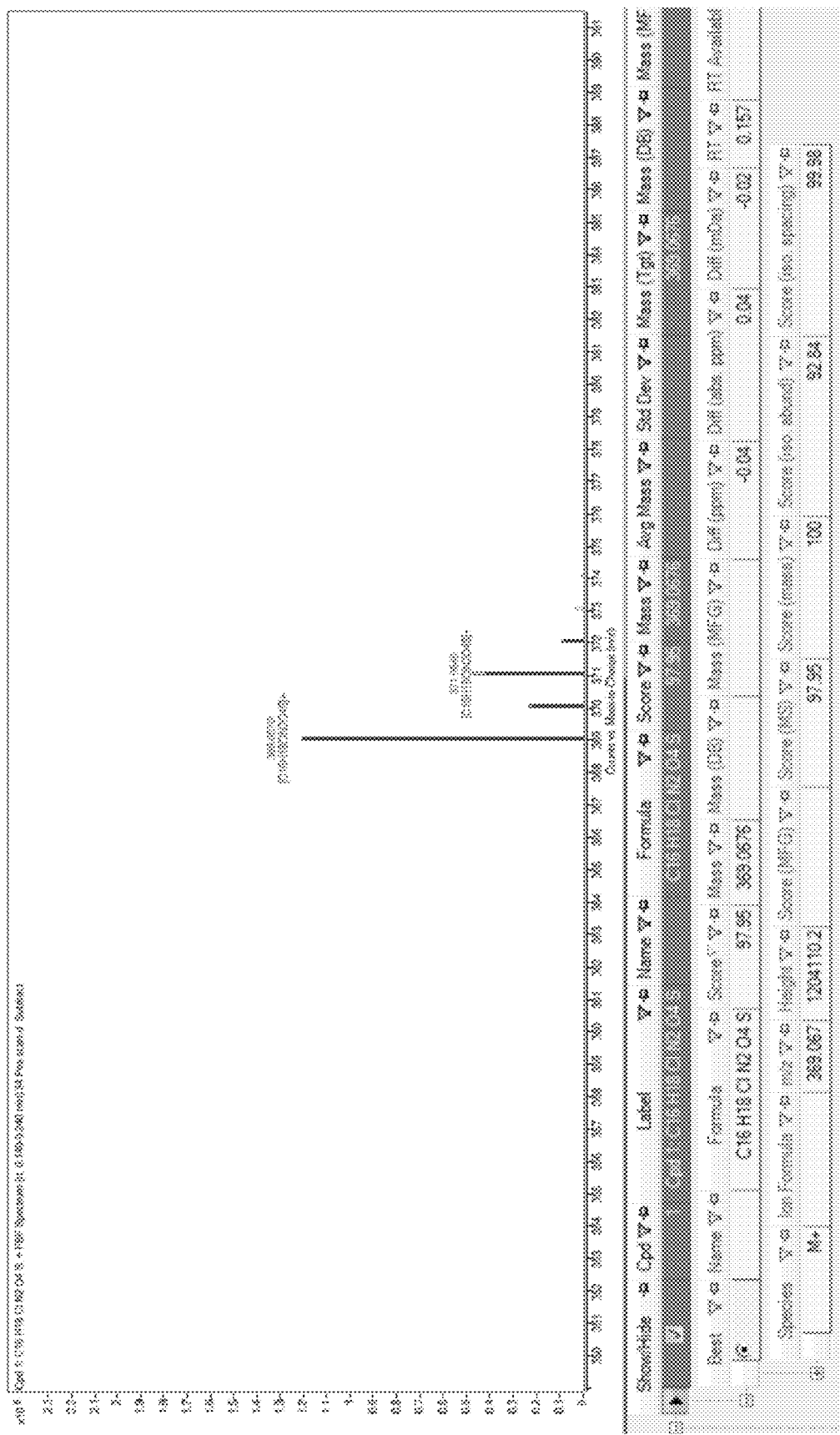

An ynamide (1a) (0.1 mmol), HNTf$_2$ (0.2 mmol), and 2-Cl-pyridine-N-oxide (0.2 mmol) were dissolved in DCE (0.2 mL), and the mixture was reacted at room temperature for 10 hours, followed by sampling. The presence or absence of the adduct was examined using Q-TOF MS. The results are shown in FIG. 7a and FIG. 7b. FIG. 7a is an enlarged view of the peaks shown in FIG. 7b.

As shown in the drawing, the Q-TOF MS analysis results confirmed the presence of an ynamide/N-oxide anion matched to the $^{35}Cl/^{37}Cl$ isotope pattern.

Figure 7C:
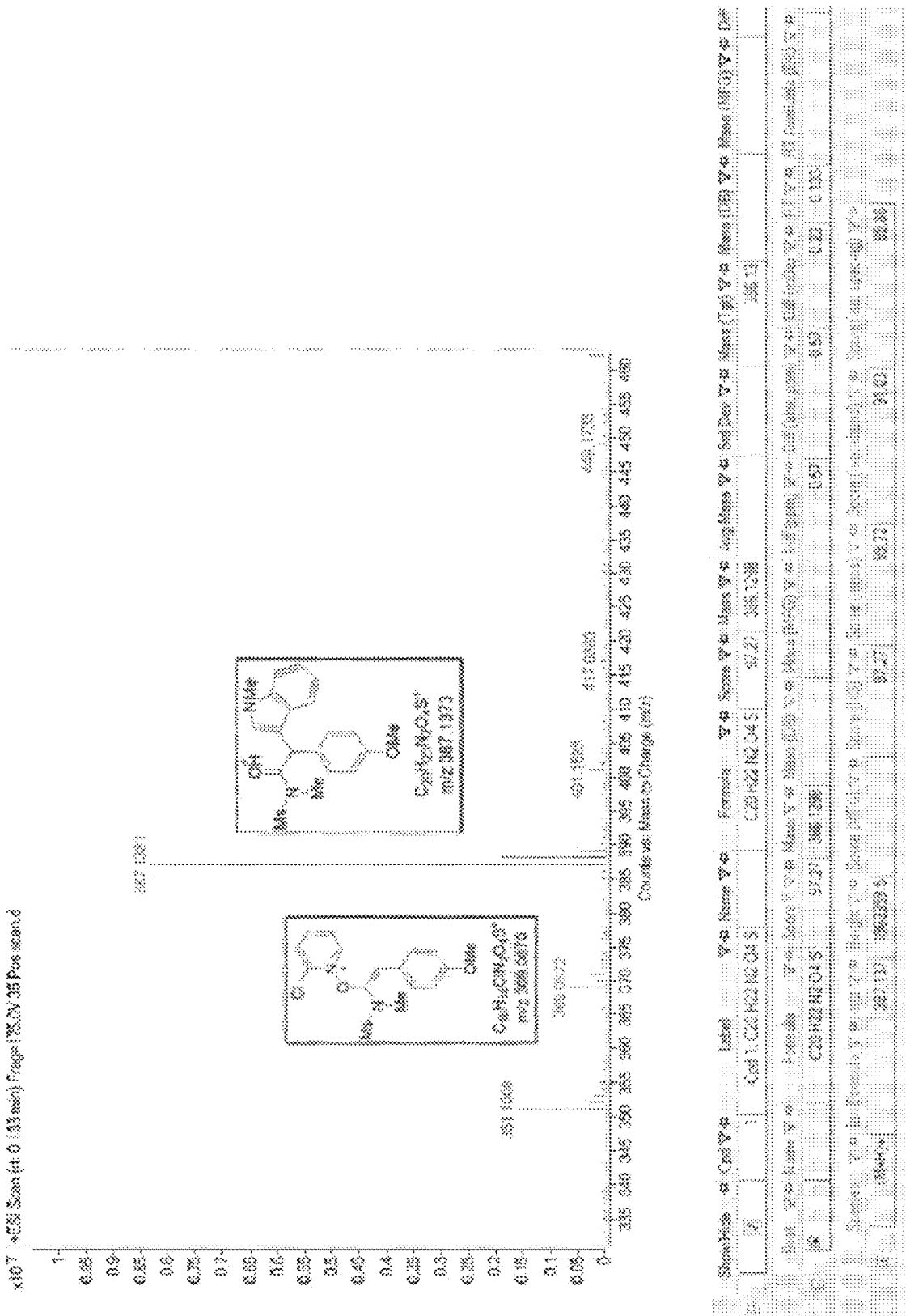

Subsequently, N-methyl indole (0.3 mmol) was added to the mixture, followed by incubation at room temperature for 5 minutes, followed by sampling and Q-TOF MS analysis. The results are shown in FIG. 7c.

As shown in the drawing, the Q-TOF MS analysis results confirmed that an ynamide/N-oxide anion and a product (3a) were formed.

Example 5

Evaluation of Rate-Determining Step

The deuteration incorporation experiment was conducted to determine the rate-determining step in the oxygenative coupling reaction according to the present disclosure.

The 3-deuterated N-methyl indole was prepared as follows:

N-Me-indole was dissolved in MeOH-d$_4$ and the mixture was treated with 5 mol % of HNTf$_2$. The solvent was removed, and the residue was partitioned between n-hexane and D$_2$O. The organic layer was separated and concentrated.

Figure 8A:
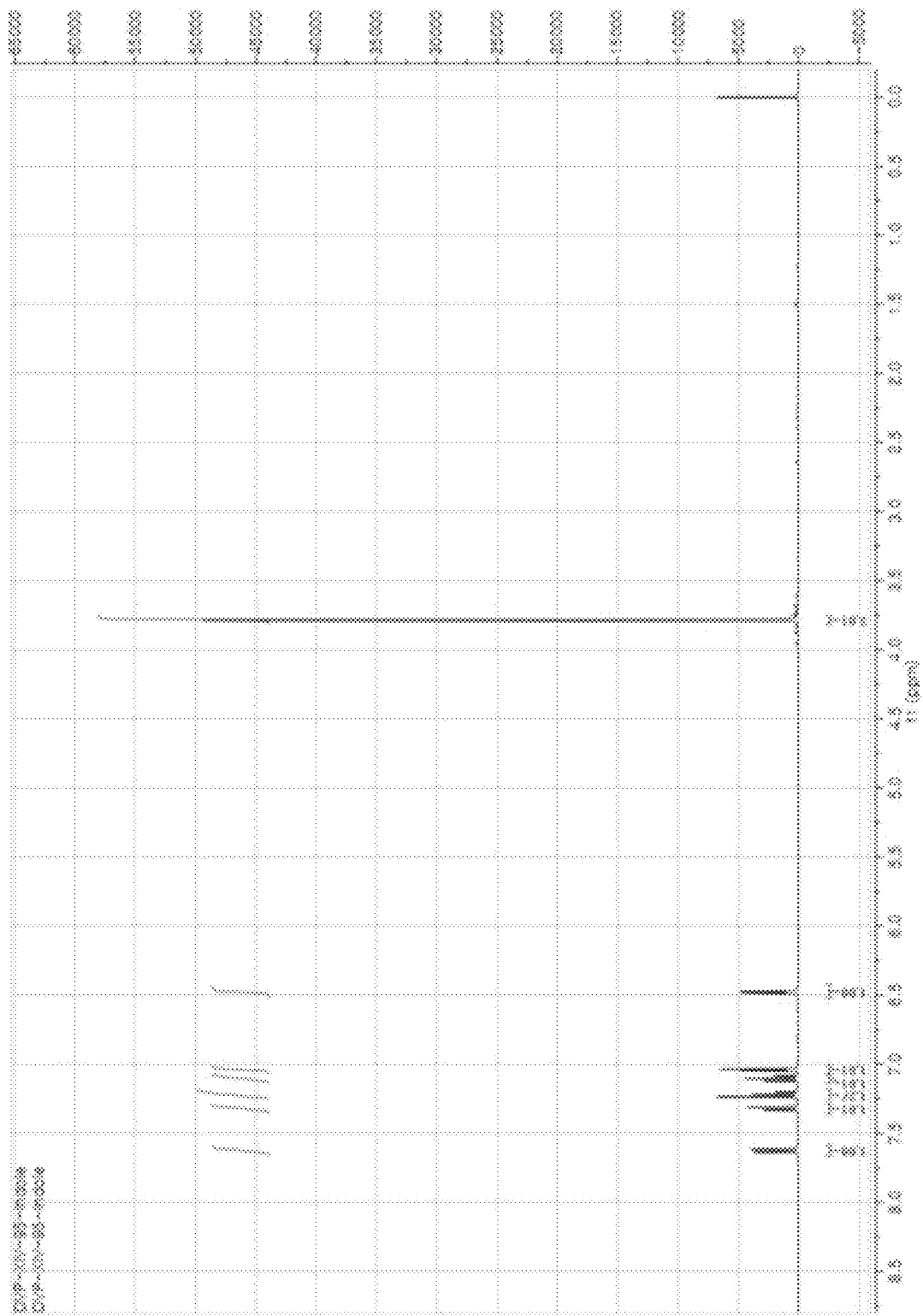
FIGS. 8a and 8b show $^1$H NMR spectra of N-Me-indole (CDCl$_3$, t1=5 ms) and 3-d-N-Me-indole (98% D, CDCl$_3$, t1=5 ms) in Example 5, respectively.
Figure 8B:
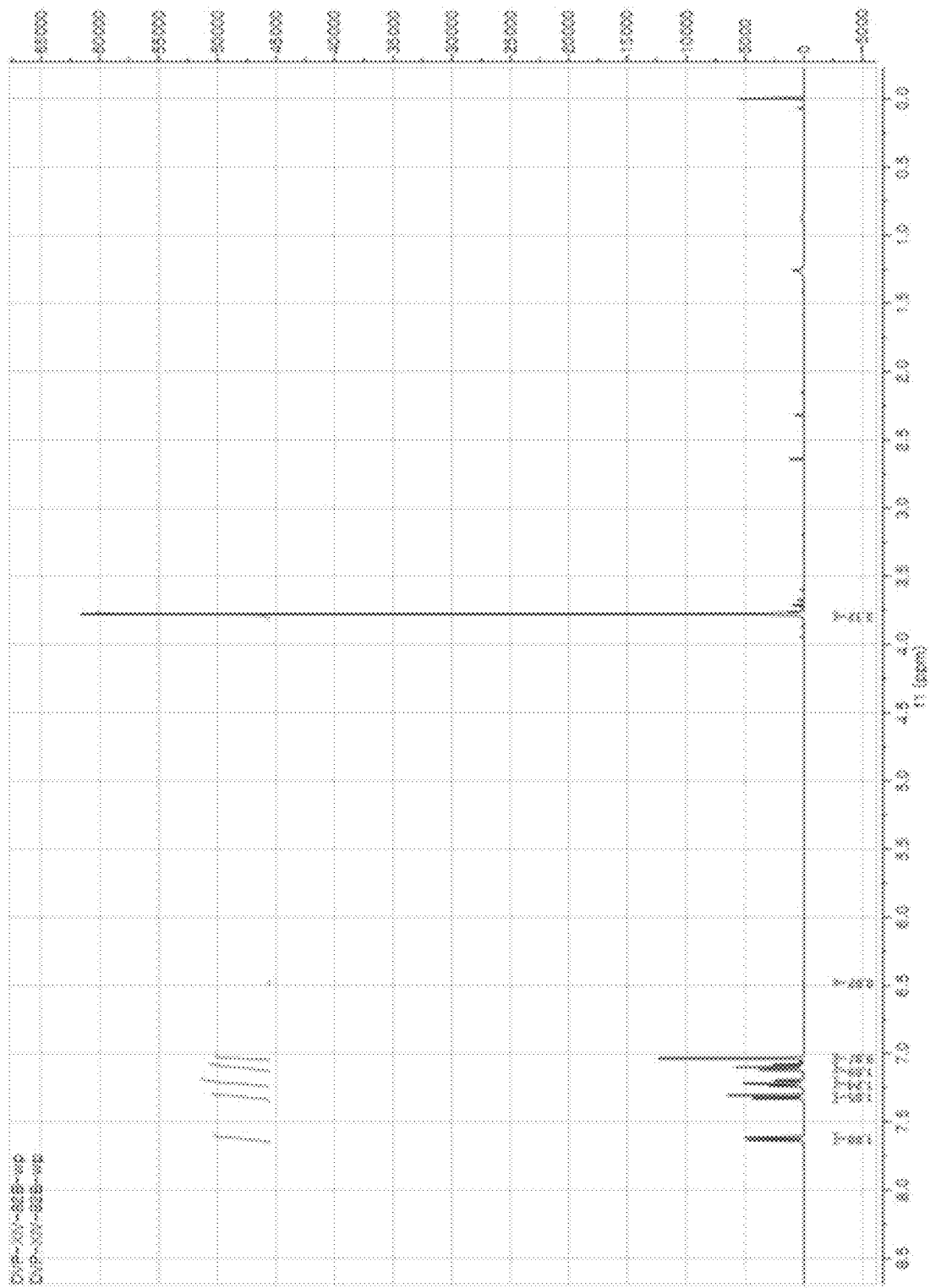

$^1$H NMR spectra of N-Me-indole (CDCl$_3$, t1=5 ms) and 3-d-N-Me-indole (98% D, CDCl$_3$, t1=5 ms) are shown in FIGS. 8a and 8b. In order to accurately quantify the amount of protons, $^1$H NMR spectrum was obtained at T1 (spin-lattice relaxation time)=5 ms.

Referring to the drawing, as a result of the $^1$H NMR analysis in CDCl$_3$, the complete deuterium exchange occurred, and such a material did not contain HNTf$_2$ as confirmed from the absence of peaks in $^{19}$F-NMR.

Figure 8C:
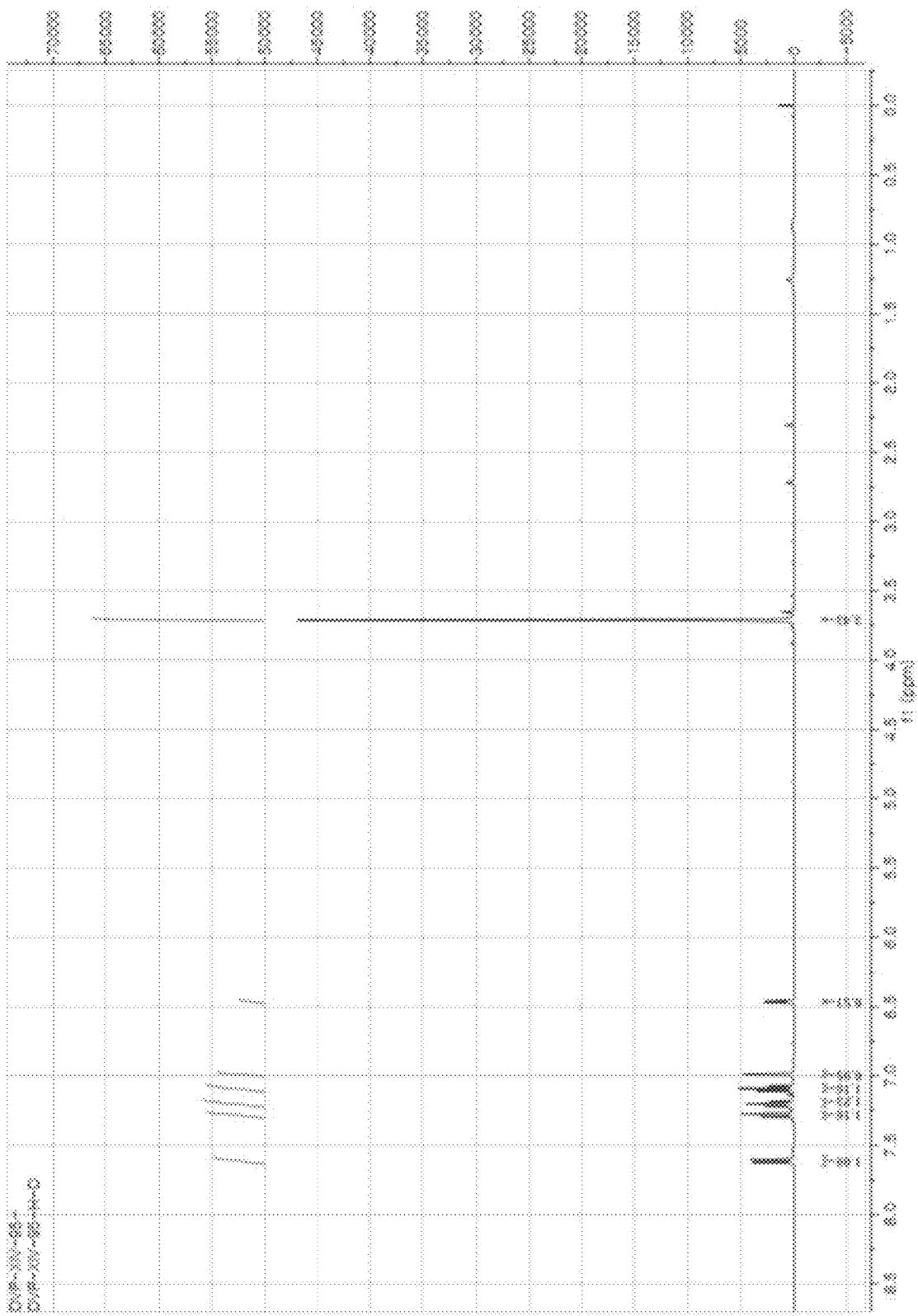
FIG. 8c shows the $^1$H NMR spectrum of the isotopic composition of a mixture composed of 300 mol % of N-Me-indole (50% D) and 5 mol % of HNTf$_2$ (50% D) in Example 5.

The proton exchange between C(3)-H of the N-Me-indole and HNTf$_2$ is rapid, and thus, the following composition was prepared by carefully mixing 3H—N-Me-indole and 3-D-N-Me-indole together with a catalytic amount of HNTf$_2$ in 1,2-DCE: 300 mol % of N-Me-indole (50% D) and 5 mol % of HNTf$_2$ (50% D). The isotopic composition of the mixture was measured by $^1$H NMR, and the results are shown in FIG. 8c (mixture of 3-H(D)-N-Me-indole (300 mol %, 49% D) and H(D)NTf$_2$ (5 mol %, 49% D)).

Thereafter, the reaction was carried out according to Reaction Scheme 17 below.

[Reaction Scheme 17]

Figure 8D:
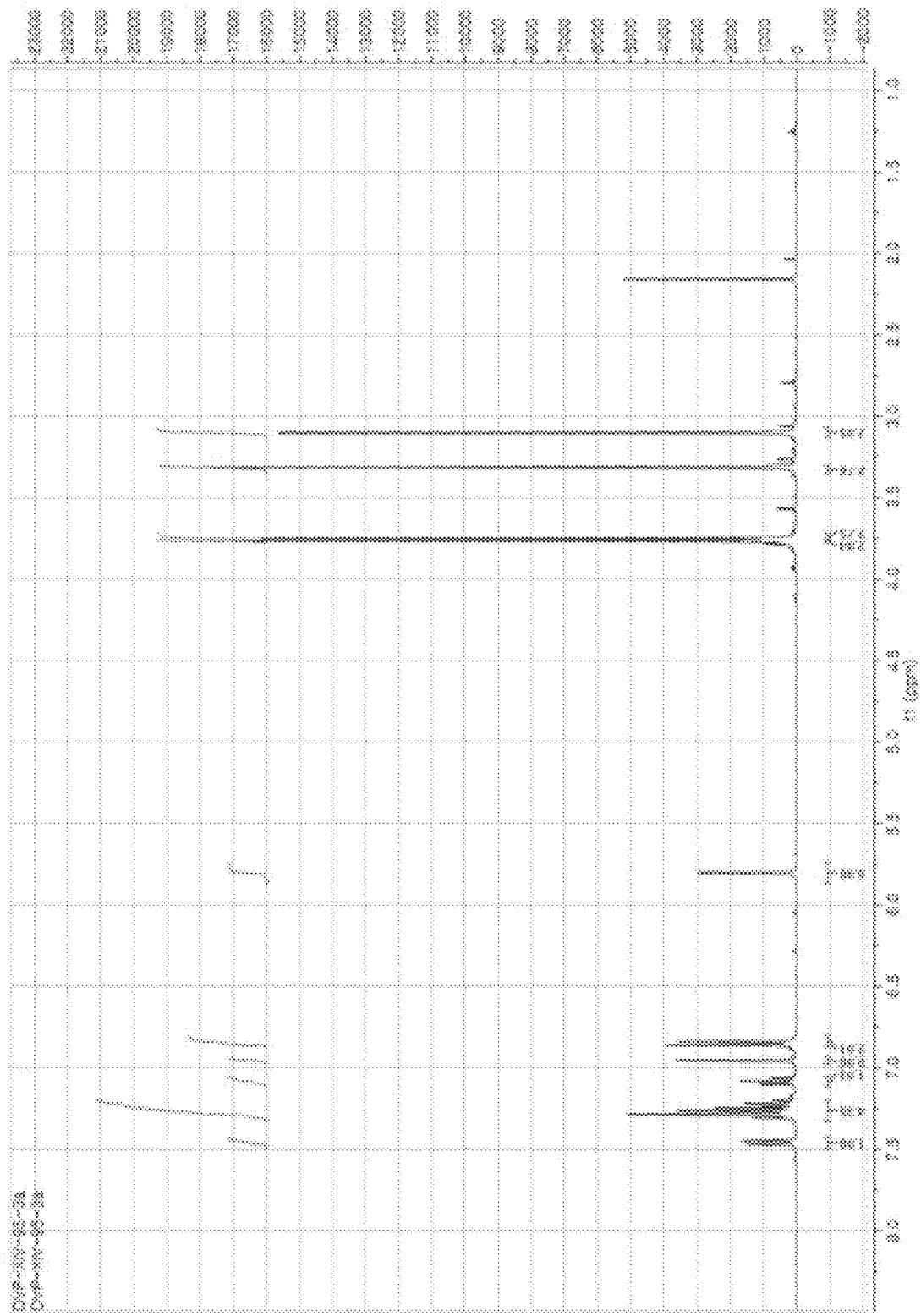
FIG. 8d shows $^1$H NMR spectrum (CDCl$_3$, t1=5 ms) of reference 3a-H in Example 5.
Figure 8E:
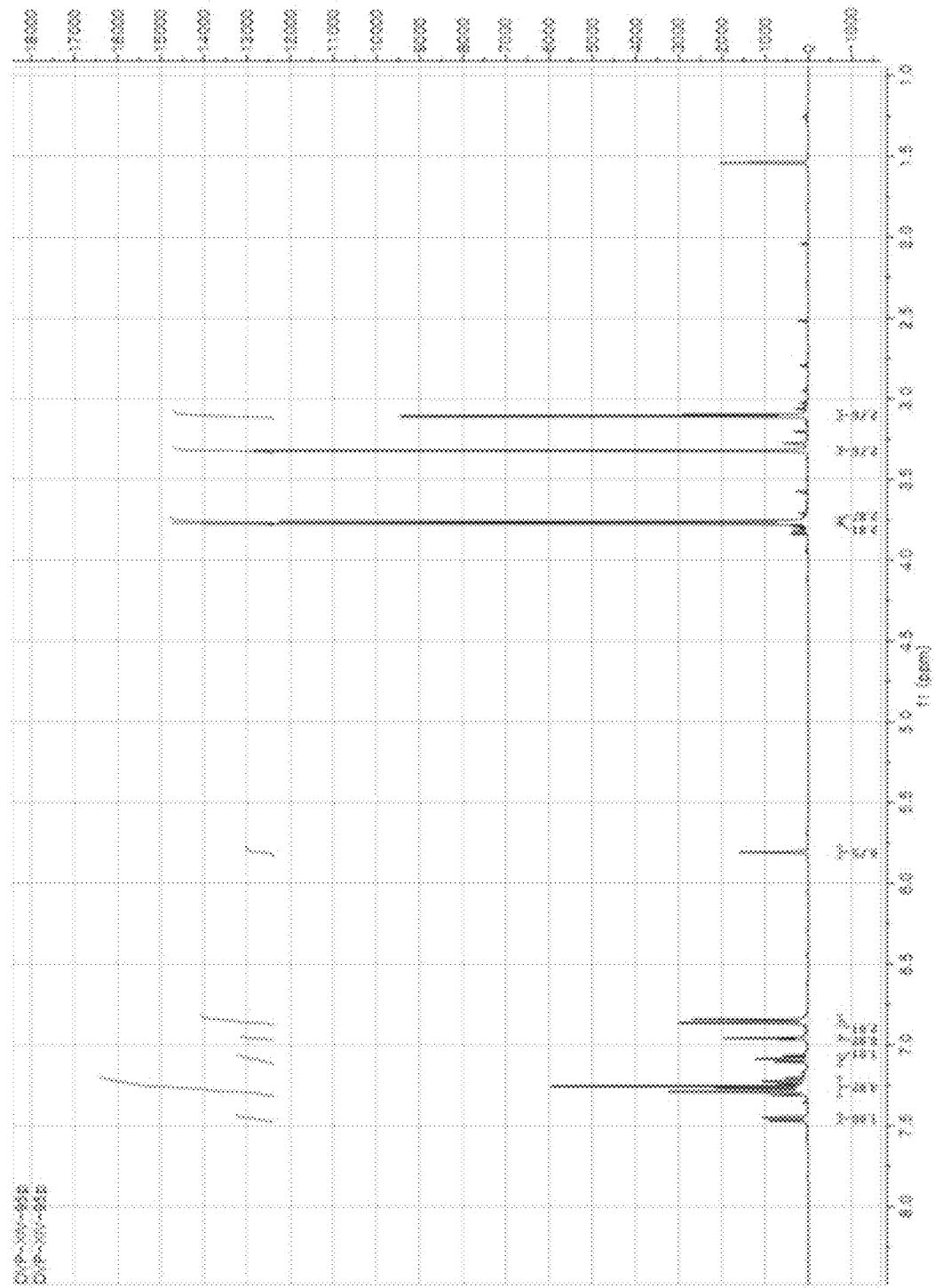
FIG. 8e shows $^1$H NMR spectrum (CDCl$_3$, t1=5 ms) of 3a-H/D from a reaction product in Example 5.

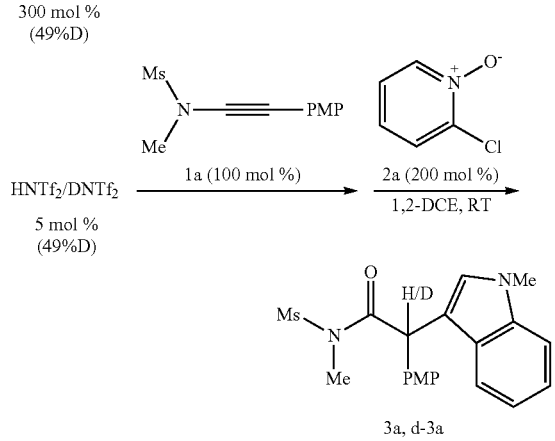

the ynamide (1a) and 2-Cl-pyridine-N-oxide (2a) were prepared by azeotropic drying with benzene prior to the reaction). After 1.5 hours at room temperature, the crude $^1$H NMR spectrum of the product (3a) was obtained. FIG. 8d shows the $^1$H NMR spectrum (CDCl$_3$, t1=5 ms) of the reference 3a-H and FIG. 8e shows the $^1$H NMR spectrum (CDCl$_3$, t1=5 ms) of the 3a-H/D from the reaction product. According to the drawing, the incorporation of deuterium into the product (3a) was 25% D.

The deuterium content in the product (3a) was the same even after chromatographic purification. Therefore, the kinetic isotope effect was obtained by integrating vinyl peaks, and the $k_H/k_D$ ratio was 3.0 (75/25). Particularly, the $k_H/k_D$ ratio was evaluated to exceed 2.3 after the calibration for the proton source from the HNTf$_2$ catalyst. Therefore, it could be confirmed that the rate-determining step was the protonation of the ynamide or the deprotonation from the initial indolyl σ-complex.

Example 6

Evaluation of Effect According to Reaction Condition Change

In the present example, in the oxygenative coupling reaction of an alkyne compound according to Reaction Scheme 18 below, the effects according to reaction conditions (the concentration of the alkyne compound in the reaction medium, the stoichiometric ratio of the reactants, the amount of the acid catalyst used, and the reaction temperature) were evaluated.

[Reaction Scheme 18]

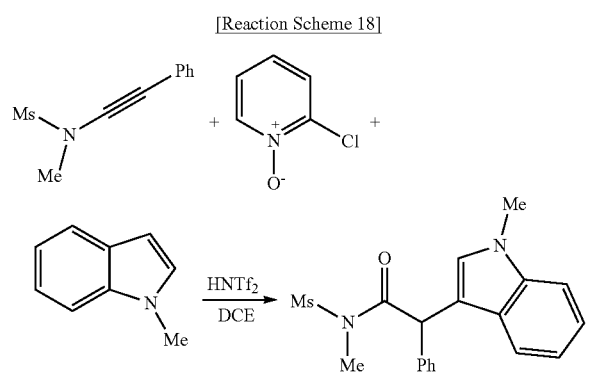

A. Effect According to Concentration of Alkyne Compound in Reaction Medium (Solvent)

The oxygenative coupling reactions was carried out while the concentration of the ynamide (molar concentration) in the reaction medium was varied (a: reaction conditions: ynamide (0.1 mmol), N-oxide (0.2 mmol), 1-methyl indole (0.3 mmol), and an acid catalyst (10 mol %) were reacted in DCE; and b: the yield was measured by $^1$H NMR spectrum using diethyl phthalate as a self-reference, and the isolated yield are shown in the parentheses). The results are shown in Table 3.

TABLE 3

| Entry | Molar concentration | Reaction conditions | Yield (%)[b] |
|---|---|---|---|
| 1 | 0.025 | RT, 21 h | 46 |
| 2 | 0.050 | RT, 10 h | 51 |
| 3 | 0.10 | RT, 7 h | 59 |

TABLE 3-continued

| Entry | Molar concentration | Reaction conditions | Yield (%)[b] |
|---|---|---|---|
| 4 | 0.20 | RT, 4 h | 70 (62) |
| 5 | 0.50 | RT, 2 h | 73 (68) |
| 6 | 0.70 | RT, 2 h | 73 |
| 7 | 0.80 | RT, 2 h | 67 |
| 8 | 1.00 | RT, 2 h | 63 |
| 9 | neat | RT, 2 h | 54 |

B. Effect According to Stoichiometric Ratio of Reactants

The oxygenative coupling reactions was carried out while the stoichiometric ratio of reactants (ynamide, N-oxide oxidant, and nucleophile) was varied (a: reaction conditions: ynamide (0.1 mmol), N-oxide (0.2 mmol), 1-methyl indole (0.3 mmol), and an acid catalyst (10 mol %) were reacted in DCE (0.5 M); and b: the yield was measured by $^1$H NMR spectrum using diethyl phthalate as a self-reference). The results are shown in Table 4.

TABLE 4

| | Equivalent | | | Reaction | |
|---|---|---|---|---|---|
| Entry | Ynamide | Oxidant | Nucleophile | conditions | Yield (%)[b] |
| 1 | 1.0 | 1.2 | 1.2 | RT, 5 h | 37 |
| 2 | 1.0 | 1.2 | 2.0 | RT, 3 h | 47 |
| 3 | 1.0 | 2.0 | 3.0 | RT, 3 h | 66 |
| 4 | 1.0 | 3.0 | 2.0 | RT, 5 h | 47 |
| 5 | 1.0 | 1.2 | 2.0 | RT, 5 h | 41 |
| 6 | 1.0 | 1.2 | 1.5 | RT, 5 h | 36 |
| 7 | 1.0 | 2.0 | 1.2 | RT, 8 h | 41 |
| 8 | 1.0 | 2.0 | 2.0 | RT, 2 h. | 60 |

C. Effect According to Amount of Acid Catalyst Used

The oxygenative coupling reaction[a] was carried out while the amount of acid catalyst used was varied (a: reaction conditions: ynamide (0.1 mmol), N-oxide (0.2 mmol), 1-methyl indole (0.3 mmol), and an acid catalyst were reacted in DCE (0.5 M); and b: the yield was measured by $^1$H NMR spectrum using diethyl phthalate as a self-reference). The results are shown in Table 5.

TABLE 5

| Entry | Amount of acid used | Reaction conditions | Yield (%)[b] |
|---|---|---|---|
| 1 | 1 mol % | RT, 4 days | 30 |
| 2 | 5 mol % | RT, 15 h | 41 |
| 3 | 10 mol % | RT, 6 h | 58 |
| 4 | 20 mol % | RT, 2 h | 69 |
| 5 | 30 mol % | RT, 2 h | 71 |

D. Effect According to Reaction Temperature

The oxygenative coupling reaction[a] was carried out while the reaction temperature was varied (a: reaction conditions: ynamide (0.1 mmol), N-oxide (0.2 mmol), 1-methyl indole (0.3 mmol), and an acid catalyst (10 mol %) were reacted in DCE (0.5 M); and b: the yield was measured by $^1$H NMR spectrum using diethyl phthalate as a self-reference). The results are shown in Table 6.

TABLE 6

| Entry | Reaction temperature | Time | Yield (%)[b] |
|---|---|---|---|
| 1 | RT | 3.5 h | 65 |
| 2 | 50° C. | 1.0 h | 60 |
| 3 | 80° C. | 1.0 h | 55 |

Accordingly, simple modifications, additions and substitutions of the present invention should also be understood as falling within the scope of the present invention, without departing from the scope and spirit of the invention as disclosed in the accompanying claims.

What is claimed is:

1. A method for oxygenative coupling of an alkyne compound, the method comprising:
reacting the alkyne compound of the following Formula 1 with a N—O bond oxidant in the presence of a Brønsted acid-containing catalyst in an organic solvent to form an alkyne-oxidant adduct intermediate; and
subsequently reacting the alkyne-oxidant adduct intermediate with a nucleophile (Nu) to form a compound of the following Formula 2:

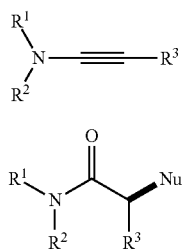

Formula 1

Formula 2 wherein, $R^1$ is carbonyl ($R^4C(O)$), sulfonyl ($R^4SO_2$), carbamate ($R^4OC(O)$), or sulfinyl ($R^4S(O)$), as a substituent that lowers electron density of N atoms, and $R^4$ is selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 alkylamine, a C3-C40 cycloalkyl group, and a heterocycloalkyl group having 3 to 40 heteronuclear atoms;

$R^2$ and $R^3$ each are independently selected from the group consisting of hydrogen, deuterium, halogen, a cyano group, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 alkylamine, a C3-C40 cycloalkyl group, and a heterocycloalkyl group having 3 to 40 heteronuclear atoms, or $R^2$ and $R^3$ may bind to a neighboring group to form a fused ring; or $R^1$ and $R^2$ may bind to each other to form an indole ring, and respective substituents at positions 2, 3, 4, 5, 6, and 7 of the indole are selected from the group consisting of a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 alkylamine, a C3-C40 cycloalkyl group, and a heterocycloalkyl group having 3 to 40 heteronuclear atoms; and Nu is any one of the following Formulas 7 to 9:

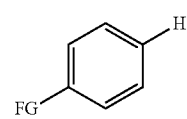

[General Formula 7]

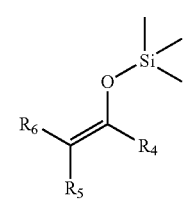

[General Formula 8]

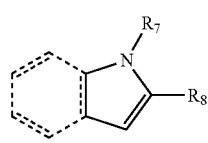

[General Formula 9]

wherein FG is an electron donating group (EDG) and is $NR_1R_2$, OH, or $OR_3$, and $R_1$ to $R_8$ each are independently selected from the group consisting of hydrogen, deuterium, a C1-C40 alkyl group, a C2-C40 alkenyl group, a C2-C40 alkynyl group, a C6-C40 aryl group, a heteroaryl group having 5 to 40 heteronuclear atoms, a C6-C40 aryloxy group, a C1-C40 alkyloxy group, a C6-C40 arylamine group, a C1-C40 alkylamine group, a C1-C40 alkyl group having C6-C40 aryl, a C1-C40 alkyl group having 1 to 6 alcohol groups, a C1-C40 alkyl group having C1-C40 alkylamine, a C3-C40 cycloalkyl group, and a heterocycloalkyl group having 3 to 40 heteronuclear atoms, or $R_1$ to $R_8$ may bind to a neighboring group to form a fused ring.

2. The method of claim 1, wherein the N—O bond oxidant is represented by the following Formula 3 or 4:

Formula 3

Formula 4 wherein R, R', and R" each are a C1-C40 heteroaryl compound that forms a ring together with N, and may also be a compound having axial chirality in which the rotation of a R'—R" bond is restricted according to the substituent.

3. The method of claim 2, wherein the N—O bond oxidant has chirality.

4. The method of claim 3, wherein the N—O bond oxidant has an S confirmation represented by the following Formula 1:

Formula 1

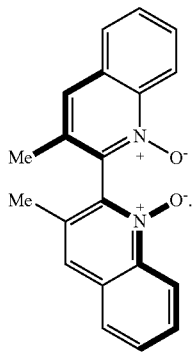

5. The method of claim 1, wherein the N—O bond oxidant is represented by the following Formula 5:

Formula 5

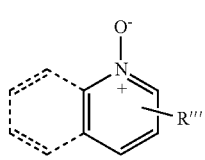

wherein R''' is hydrogen, a halogen, a dihalogen, a cyano group, an alkoxy group, or a nitro group.

6. The method of claim 5, wherein R''' is hydrogen, 2-chloro, 2-bromo, 2-methoxy, 4-nitro, 2,4-dichloro, 2,6-dichloro, 2,6-dibromo or 3,5-dibromo.

7. The method of claim 1, wherein the oxygenative coupling is performed through a single stage.

8. The method of claim 1, wherein the Brønsted acid exhibits acidity with an acid dissociation constant (pKa) in the range of −10 to 7 in an aqueous solution.

9. The method of claim 8, wherein the Brønsted acid is selected, according to the structure of a counter anion, from the group consisting of (i) conjugate acids of sulfonate, bis-sulfonimide, phosphate, phosphoramide, or carboxylate, for oxygen acids and nitrogen acids; (ii) conjugate acids of carbanions with aryl groups attached thereto, the aryl groups comprising one to three $CF_3$, $C_6F_5$, $SO_2CF_3$, $SO_2C_6F_5$ groups and three to five F atoms, for carbonic acids; and (iii) a combination thereof.

10. The method of claim 1, wherein the Brønsted acid is at least one selected from the group consisting of HCl, $HBF_4$, and $HSbF_6$.

11. The method of claim 1, wherein the organic solvent is at least one selected from the group consisting of: a chlorine-based solvent containing C1-C5 aliphatic hydrocarbons with 1 to 5 chlorine atoms; a solvent containing a C6-C10 aromatic hydrocarbon; a solvent containing a C5-C10 aliphatic hydrocarbon; and a solvent containing a C1-C8 alcohol, amino, nitrile, and/or nitro groups.

12. The method of claim 1, wherein the organic solvent is at least one selected from the group consisting of dichloroethane, dichloromethane, chloroform (trichloromethane), chlorobenzene, 1,2-dichlorobenzene, 1,1,2,2-tetrachloroethane, 1,1,2-trichloroethane, 1,2,3-trichloropropane, 1,1,2,2-tetrachlorethylene, methanol, acetonitrile, toluene, ether, and hexane.

13. The method of claim 1, wherein the amount of the Brønsted acid-containing catalyst relative to the alkyne compound is 1-40 mol %.

14. The method of claim 1, wherein the equivalent ratio of the N—O bond oxidant to the alkyne compound is in the range of 0.9 to 3.

15. The method of claim 1, wherein the equivalent ratio of the nucleophile to the alkyne compound is in the range of 1 to 3.5.

16. The method of claim 1, wherein the oxygenative coupling is performed at 15-50° C.

17. The method of claim 1, wherein the oxygenative coupling is performed at 20-30° C.

18. The method of claim 1, wherein the concentration of the alkyne compound in the organic solvent is in the range of 0.05-1 M.

* * * * *